(12) United States Patent
Sasaki et al.

(10) Patent No.: US 12,593,985 B2
(45) Date of Patent: Apr. 7, 2026

(54) IMAGE PROCESSING APPARATUS, IMAGE PROCESSING METHOD, AND NON-TRANSITORY COMPUTER-READABLE MEDIUM

(71) Applicants: CANON KABUSHIKI KAISHA, Tokyo (JP); KEIO UNIVERSITY, Tokyo (JP)

(72) Inventors: Shoya Sasaki, Kanagawa (JP); Kenichi Nagae, Kanagawa (JP); Hiroki Kajita, Tokyo (JP); Nobuaki Imanishi, Tokyo (JP); Sadakazu Aiso, Tokyo (JP)

(73) Assignees: Canon Kabushiki Kaisha, Tokyo (JP); Luxonus Inc., Kawasaki (JP)

( * ) Notice: Subject to any disclaimer, the term of this patent is extended or adjusted under 35 U.S.C. 154(b) by 749 days.

(21) Appl. No.: 17/178,403

(22) Filed: Feb. 18, 2021

(65) Prior Publication Data

US 2021/0177268 A1     Jun. 17, 2021

Related U.S. Application Data

(63) Continuation of application No. PCT/JP2019/013940, filed on Mar. 29, 2019.

(30) Foreign Application Priority Data

Aug. 21, 2018     (JP) ................................ 2018-155033

(51) Int. Cl.
*A61B 5/00* (2006.01)

(52) U.S. Cl.
CPC .......... *A61B 5/0095* (2013.01); *A61B 5/0075* (2013.01); *A61B 5/742* (2013.01); *A61B 2576/00* (2013.01)

(58) Field of Classification Search
CPC .............................. A61B 5/0095; A61B 8/481
See application file for complete search history.

(56) References Cited

U.S. PATENT DOCUMENTS

| | | | |
|---|---|---|---|
| 7,945,018 B2 | 5/2011 | Heismann | |
| 10,765,324 B2 | 9/2020 | Irisawa | |

(Continued)

FOREIGN PATENT DOCUMENTS

| | | |
|---|---|---|
| CN | 101036582 A | 9/2007 |
| JP | 2017-023705 A | 2/2017 |

(Continued)

OTHER PUBLICATIONS

Sep. 22, 2023 Chinese Official Action in Chinese Patent Appln. No. 201980054755.0.

(Continued)

*Primary Examiner* — Rajeev P Siripurapu
(74) *Attorney, Agent, or Firm* — Venable LLP

(57) ABSTRACT

An image processing apparatus includes a spectral image acquisition unit configured to acquire a spectral image that is an image generated using photoacoustic signals corresponding to a plurality of different wavelengths, based on photoacoustic waves generated by radiating lights with the plurality of different wavelengths to an object into which a contrast agent has been injected, a contrast agent information acquisition unit configured to acquire information about the contrast agent, a region determination unit configured to determine a region corresponding to the contrast agent in the spectral image on the basis of the information about the contrast agent, and a display control unit configured to display the spectral image such that the region corresponding to the contrast agent is distinguishable from a region other than the region corresponding to the contrast agent.

31 Claims, 13 Drawing Sheets

(56) References Cited

U.S. PATENT DOCUMENTS

| | | | |
|---|---|---|---|
| 2008/0221647 A1* | 9/2008 | Chamberland | A61N 5/062 |
| | | | 382/131 |
| 2009/0156932 A1* | 6/2009 | Zharov | A61B 5/412 |
| | | | 600/437 |
| 2010/0220834 A1 | 9/2010 | Heismann | |
| 2012/0123256 A1* | 5/2012 | Razansky | A61B 5/0095 |
| | | | 600/407 |
| 2013/0144150 A1* | 6/2013 | Kim | A61B 8/0816 |
| | | | 600/407 |
| 2013/0225951 A1 | 8/2013 | Khoobehi | |
| 2013/0304405 A1* | 11/2013 | Schmid | A61B 5/0095 |
| | | | 702/56 |
| 2014/0163353 A1* | 6/2014 | Razansky | A61B 5/0095 |
| | | | 600/407 |
| 2014/0182384 A1* | 7/2014 | Watanabe | G01N 21/1702 |
| | | | 73/655 |
| 2014/0198606 A1* | 7/2014 | Morscher | G01N 21/1702 |
| | | | 367/7 |
| 2015/0160120 A1 | 6/2015 | Sun et al. | |
| 2017/0325693 A1 | 11/2017 | Fukui et al. | |
| 2018/0055370 A1 | 3/2018 | Takahashi et al. | |
| 2018/0132729 A1* | 5/2018 | Irisawa | A61B 8/5246 |
| 2018/0177405 A1* | 6/2018 | Sasaguri | A61B 5/14535 |
| 2019/0117197 A1* | 4/2019 | Cheng | A61B 8/5223 |
| 2019/0216436 A1 | 7/2019 | Miyazawa et al. | |

FOREIGN PATENT DOCUMENTS

| | | | |
|---|---|---|---|
| JP | 2017-202319 A | 11/2017 |
| JP | 2018-057697 A | 4/2018 |
| WO | 2011/137115 A1 | 11/2011 |
| WO | 2017/002337 A1 | 1/2017 |
| WO | 2017/014167 A1 | 1/2017 |

OTHER PUBLICATIONS

CN 101036582 A, US 2010/0220834 A1, U.S. Pat. No. 7,945,018 B2.
JP 2017-023705 A, US 2018/0177405 A1.
WO 2011/137115 A1, US 2013/0225951 A1.
Jun. 18, 2019 International Search Report in International Patent Appln. No. PCT/JP2019/013940.
Apr. 11, 2022 Extended European Search Report in International Patent Appln. No. PCT/JP2019/013940 (11 pages).
Yusuke Shigeta, et al., "Multispectral photoacoustic characterization of ICG and porcine blood using an LED-based photoacoustic imaging system," ResearchGate, https://www.researchgate.net/publication/328232932, from Conference:SPIE BiOS Photonics West 2018, Jan. 2018.

* cited by examiner

LIGHT
SOURCE

ICG 2.5mg/mL

BEFORE ICG
INJECTION

ICG 5mg/mL

ICG 1.0mg/mL

ICG 5mg/mL

ICG 0.5mg/mL

IMAGE PROCESSING APPARATUS, IMAGE PROCESSING METHOD, AND NON-TRANSITORY COMPUTER-READABLE MEDIUM

CROSS-REFERENCE TO RELATED APPLICATIONS

This application is a Continuation of International Patent Application No. PCT/JP2019/013940, filed Mar. 29, 2019, which claims the benefit of Japanese Patent Application No. 2018-155033, filed Aug. 21, 2018, both of which are hereby incorporated by reference herein in their entirety.

BACKGROUND OF THE INVENTION

Field of the Invention

The present invention relates to image processing for images generated by photoacoustic imaging.

Description of the Related Art

In examination of blood vessels and lymphatic vessels, photoacoustic imaging (also called "optical ultrasonic imaging") using a contrast agent is known. PTL 1 discloses a photoacoustic image generation device that uses a contrast agent used for contrasting of lymph nodes, lymphatic vessels, and the like as an evaluation target and projects light with a wavelength which is absorbed by the contrast agent to generate photoacoustic waves.

However, there are cases in which it is difficult to ascertain a structure of a contrasting target in an object (e.g., running in blood vessels, lymphatic vessels, and the like) in the photoacoustic imaging disclosed in PTL 1.

Accordingly, an object of the present invention is to provide an image processing apparatus for generating a display image through which a structure of a contrasting target is easily ascertained through photoacoustic imaging.

CITATION LIST

Patent Literature

PTL 1 International Publication Pamphlet No. WO 2017/002337

SUMMARY OF THE INVENTION

An image processing apparatus according to one aspect of the present invention includes a spectral image acquisition unit configured to acquire a spectral image that is an image generated using photoacoustic signals corresponding to a plurality of different wavelengths, based on photoacoustic waves generated by radiating lights with the plurality of different wavelengths to an object into which a contrast agent has been injected, a contrast agent information acquisition unit configured to acquire information about the contrast agent, a region determination unit configured to determine a region corresponding to the contrast agent in the spectral image on the basis of the information about the contrast agent, and a display control unit configured to display the spectral image such that the region corresponding to the contrast agent is distinguishable from a region other than the region corresponding to the contrast agent.

Further features of the present invention will become apparent from the following description of exemplary embodiments with reference to the attached drawings.

DESCRIPTION OF THE EMBODIMENTS

Figure 1:
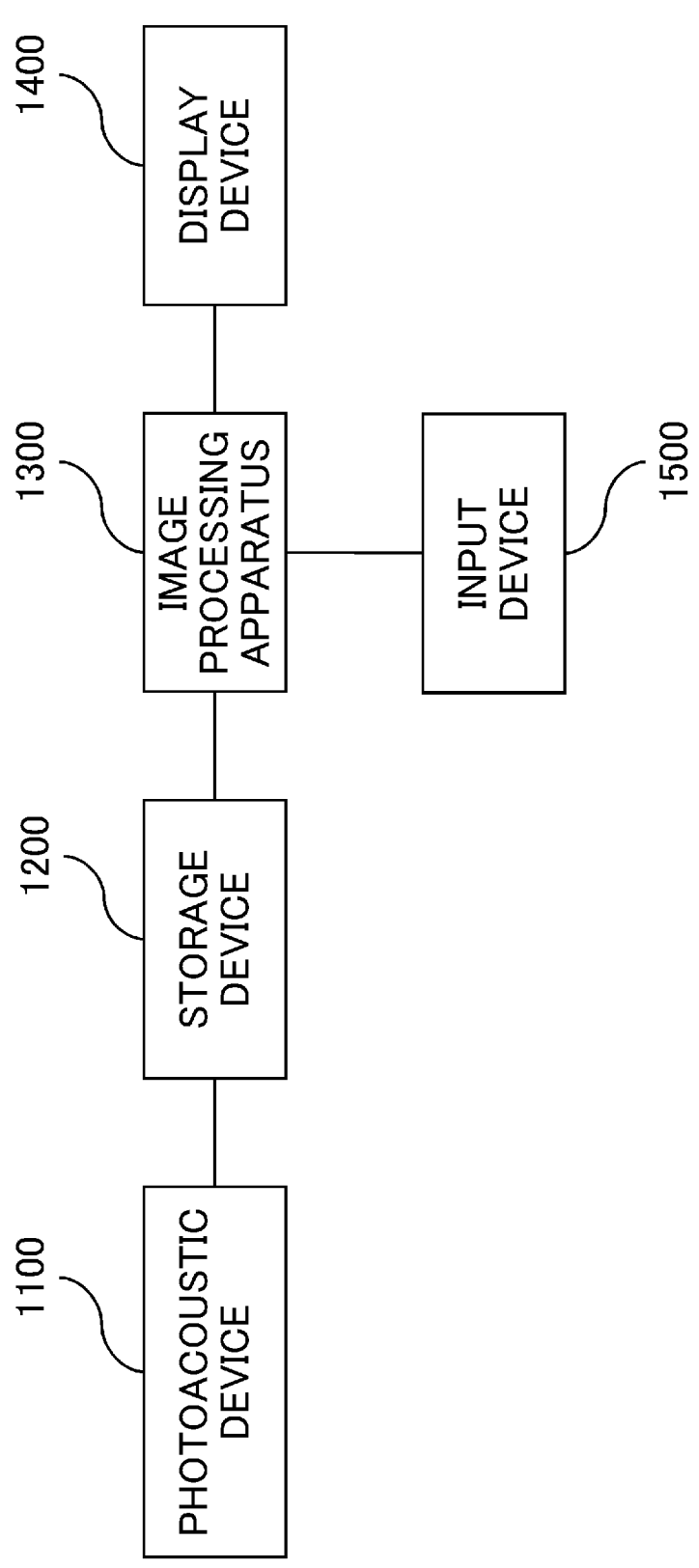
FIG. 1 is a block diagram of a system according to an embodiment of the present invention.

Hereinafter, suitable embodiments of the present invention will be described with reference to the drawings. However, dimensions, materials, shapes, a relative arrangement, and the like of components described below may be appropriately changed according to a configuration of a device to which the invention is applied and various conditions. Accordingly, the scope of the present invention is not limited to the following description.

A photoacoustic image acquired by a system according to the present invention reflects an absorption amount and an absorption rate of optical energy. A photoacoustic image is an image representing a spatial distribution of at least one piece of object information including a photoacoustic wave generating sound pressure (initial sound pressure), a light absorption energy density, a light absorption coefficient, and the like. A photoacoustic image may be an image representing a two-dimensional spatial distribution or an image (volume data) representing a three-dimensional spatial distribution. The system according to the present embodiment generates a photoacoustic image by imaging an object into which a contrast agent is injected. Meanwhile, to ascertain a three-dimensional structure of a contrasting target, a photoacoustic image may be an image representing a two-dimensional spatial distribution in a depth direction from the surface of an object or an image representing a three-dimensional spatial distribution.

In addition, the system according to the present invention can generate a spectral image of an object using a plurality of photoacoustic images corresponding to a plurality of wavelengths. A spectral image of the present invention is an image generated using photoacoustic signals corresponding to a plurality of wavelengths based on photoacoustic waves generated by radiating lights with a plurality of different wavelengths to an object.

Meanwhile, a spectral image may be an image representing a concentration of a specific material in an object, which is generated using photoacoustic signals corresponding to a plurality of wavelengths. When a light absorption coefficient spectrum of a contrast agent to be used is different from a light absorption coefficient spectrum of the specific material, an image value of the contrast agent in the spectral image is different from an image value of the specific material in the spectral image. Accordingly, a region of the contrast agent can be distinguished from a region of the specific material according to image values of the spectral image. Meanwhile, as the specific material, a material constituting an object, such as hemoglobin, glucose, collagen, melanin, fat, or water, is conceivable. In this case, it is necessary to select a contrast agent having a light absorption spectrum different from the light absorption coefficient spectrum of the specific material. In addition, a spectral image may be calculated through different calculation methods depending on types of specific materials.

In an embodiment which will be described below, an image calculated using an oxygen saturation calculation formula (1) will be described as a spectral image. The inventors found that a calculated value $Is(r)$ greatly deviating from a numerical value range that can be taken by an oxygen saturation of hemoglobin was obtained when a measured value $I(r)$ of a photoacoustic signal acquired using a contrast agent in which wavelength dependence of a light absorption coefficient tends to be different from those of oxyhemoglobin and deoxyhemoglobin was put into the formula (1) for calculating the oxygen saturation (an index having a correlation with the oxygen saturation is possible) of hemoglobin in the blood on the basis of photoacoustic signals corresponding to a plurality of wavelengths. Therefore, if a spectral image is generated using the calculated value $Is(r)$ as an image value, it is easy to separate (distinguish) a region of hemoglobin (blood vessel region) from a contrast agent existing region (e.g., a lymphatic vessel region if the contrast agent is injected into lymphatic vessels) in the object on an image.

[Math. 1]

$$Is(r) = \frac{\frac{I^{\lambda_2}(r)}{I^{\lambda_1}(r)} \cdot \varepsilon_{Hb}^{\lambda_1} - \varepsilon_{Hb}^{\lambda_2}}{\left(\varepsilon_{HbO}^{\lambda_2} - \varepsilon_{Hb}^{\lambda_2}\right) - \frac{I^{\lambda_2}(r)}{I^{\lambda_1}(r)} \cdot \left(\varepsilon_{HbO}^{\lambda_1} - \varepsilon_{Hb}^{\lambda_1}\right)} \quad \text{formula (1)}$$

Here, $I^{\lambda_1}(r)$ is a measured value based on photoacoustic waves generated according to radiation of light with a first wavelength $\lambda_1$ and $I^{\lambda_2}(r)$ is a measured value based on photoacoustic waves generated according to radiation of light with a second wavelength $\lambda_2$. $\varepsilon_{Hb}^{\lambda_1}$ is a molar absorption coefficient [mm$^{-1}$ mol$^{-1}$] of deoxyhemoglobin corresponding to the first wavelength $\lambda_1$ and $\varepsilon_{Hb}^{\lambda_2}$ is a molar absorption coefficient [mm$^{-1}$ mol$^{-1}$] of deoxyhemoglobin corresponding to the second wavelength $\lambda_2$. $\varepsilon_{HbO}^{\lambda_1}$ is a molar absorption coefficient [mm$^{-1}$ mol$^{-1}$] of oxyhemoglobin corresponding to the first wavelength $\lambda_1$ and $\varepsilon_{HbO}^{\lambda_2}$ is a molar absorption coefficient [mm$^{-1}$ mol$^{-1}$] of oxyhemoglobin corresponding to the second wavelength $\lambda_2$. $r$ is a position. Meanwhile, as the measured value $I^{\lambda_1}(r)$ and $I^{\lambda_2}(r)$, absorption coefficients $\mu_a^{\lambda_1}(r)$ and $\mu_a^{\lambda_2}(r)$ may be used or initial sound pressures $P_0^{\lambda_1}(r)$ and $P_0^{\lambda_2}(r)$ may be used.

When a measured value based on photoacoustic waves generated from a hemoglobin existing region (blood vessel region) is put into formula (1), the oxygen saturation (or an index having a correlation with the oxygen saturation) of hemoglobin is acquired as the calculated value $Is(r)$. On the other hand, in the object into which the contrast agent has been injected, when a measured value based on acoustic waves generated from a contrast agent existing region (e.g., a lymphatic vessel region) is put into formula (1), a pseudo-concentration distribution of the contrast agent is acquired as the calculated value $Is(r)$. Meanwhile, when the concentration distribution of the contrast agent is calculated, the numerical value of the molar absorption coefficient of hemoglobin may be used as it is in formula (1). The spectral image $Is(r)$ acquired in this manner becomes an image drawn in a state in which both a hemoglobin existing region (blood vessels) and a contrast agent existing region (e.g., lymphatic vessels) in the object can be separated (distinguished) from each other.

Meanwhile, although an image value of a spectral image is calculated using formula (1) for calculating an oxygen saturation in the present embodiment, a calculation method other than formula (1) may be used when an index other than the oxygen saturation is calculated as an image value of a spectral image. Since known indexes and index calculation methods can be used as the index and a method of calculating the same, detailed description thereof is omitted here.

In addition, the system according to the present invention may use, as a spectral image, an image representing a ratio of a first photoacoustic image based on photoacoustic waves generated according to radiation of light with the first wavelength $\lambda_1$ to a second photoacoustic image based on photoacoustic waves generated according to radiation of light with the second wavelength $\lambda_2$. That is, an image based on the ratio of the first photoacoustic image based on photoacoustic waves generated according to radiation of light with the first wavelength $\lambda_1$ to the second photoacoustic image based on photoacoustic waves generated according to radiation of light with the second wavelength $\lambda_2$ may be used as a spectral image. Meanwhile, an image generated according to a modified formula of formula (1) can also be expressed by the ratio of the first photoacoustic image to the second photoacoustic image and thus can be said to be an image (spectral image) based on the ratio of the first photoacoustic image to the second photoacoustic image.

Meanwhile, to ascertain a three-dimensional structure of a contrasting target, a spectral image may be a two-dimensional spatial distribution or a three-dimensional spatial distribution in a depth direction from the surface of an object.

Hereinafter, a configuration of the system and an image processing method of the present embodiment will be described.

The system according to the present embodiment will be described using FIG. 1. FIG. 1 is a block diagram illustrating a configuration of the system according to the present embodiment. The system according to the present embodiment includes a photoacoustic device 1100, a storage device 1200, an image processing apparatus 1300, a display device 1400, and an input device 1500. Transmission and reception of data between devices may be performed in a wired or wireless manner.

The photoacoustic device 1100 generates a photoacoustic image by imaging an object into which a contrast agent has been injected and outputs the photoacoustic image to the storage device 1200. The photoacoustic device 1100 is a device that generates information of characteristic values corresponding to a plurality of positions in the object using a received signal acquired by receiving photoacoustic waves generated according to radiation of light. That is, the photoacoustic device 1100 is a device that generates a spatial distribution of characteristic value information derived from photoacoustic waves as medical image data (photoacoustic image).

The storage device 1200 may be a storage medium such as a read only memory (ROM), a magnetic disk, or a flash memory. In addition, the storage device 1200 may be a storage server via a network such as a picture archiving and communication system (PACS).

The image processing apparatus 1300 is a device that processes information such as photoacoustic images and supplementary information of photoacoustic images stored in the storage device 1200.

Units that execute an arithmetic operation function of the image processing apparatus 1300 can be composed of a processor such as a CPU or a graphics processing unit (GPU), and an arithmetic operation circuit such as a field programmable gate array (FPGA). These units may be composed of not only a single processor and a single arithmetic operation circuit but also a plurality of processors and a plurality of arithmetic operation circuits.

A unit that executes a storage function of the image processing apparatus 1300 can be configured as a non-transient storage medium such as a read only memory (ROM), a magnetic disk or a flash memory. In addition, the unit that executes the storage function may be a volatile medium such as a random access memory (RAM). Meanwhile, a storage medium in which programs are stored is a non-transient storage medium. Further, the unit that executes the storage function may be configured as not only a single storage medium but also a plurality of storage media.

A unit that executes a control function of the image processing apparatus 1300 is configured as an arithmetic operation element such as a CPU. The unit that executes the control function controls the operation of each component of the system. The unit that executes the control function may receive instruction signals according to various operations such as starting of measurement from an input unit and control each component of the system. In addition, the unit that executes the control function may read program code stored in a computer 150 and control the operation of each component of the system.

The display device 1400 is a display such as a liquid crystal display or an organic electroluminescence (EL) device. In addition, the display device 1400 may display a GUI for operating images or devices.

As the input device 1500, an operation console composed of a mouse, a keyboard, and the like that can be operated by a user can be used. In addition, the display device 1400 may be configured as a touch panel and the display device 1400 may be used as the input device 1500.

Figure 2:
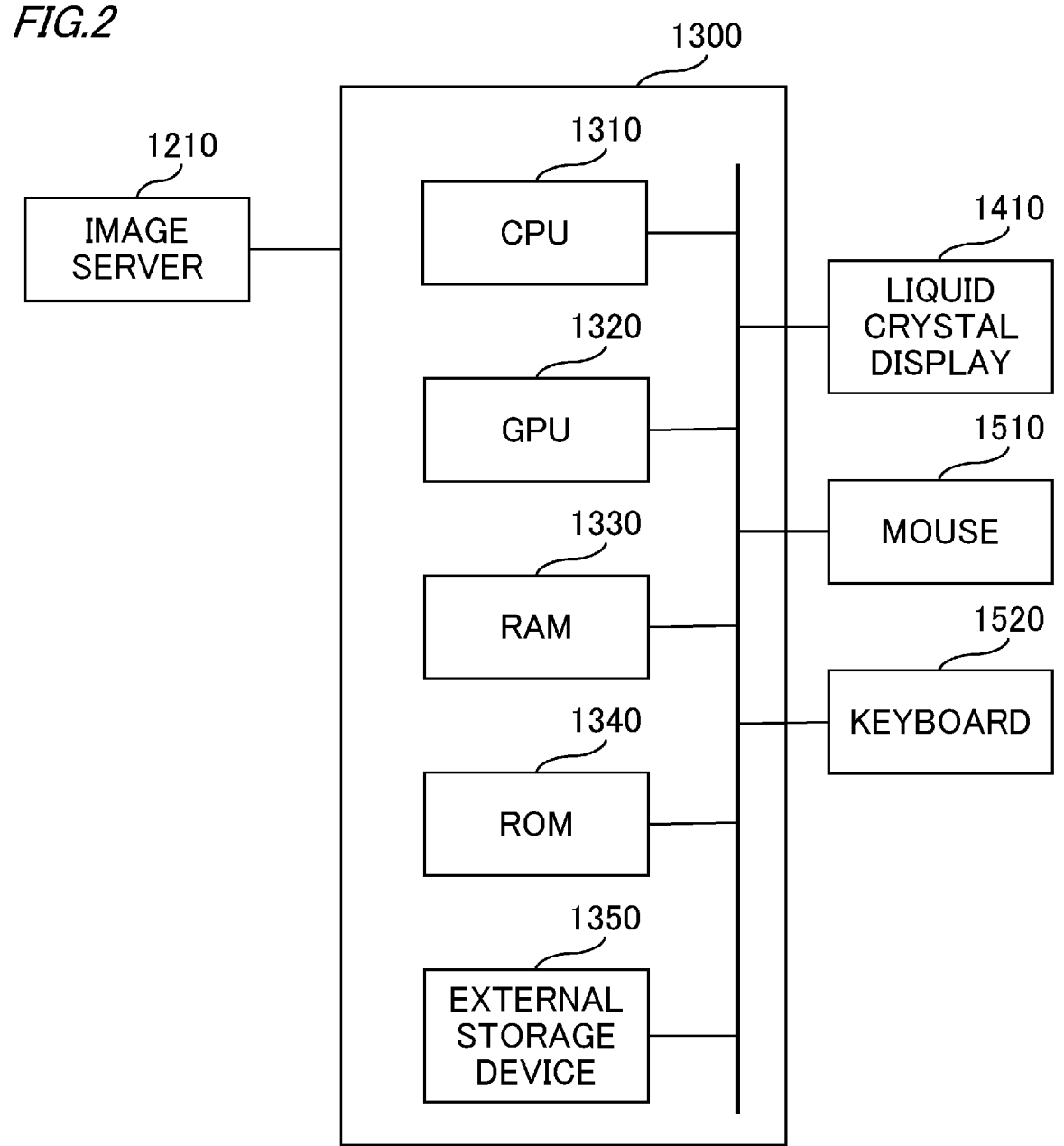
FIG. 2 is a block diagram illustrating a specific example of an image processing apparatus and peripheral components thereof according to an embodiment of the present invention.

FIG. 2 illustrates a specific configuration example of the image processing apparatus 1300 according to the present embodiment. The image processing apparatus 1300 according to the present embodiment includes a CPU 1310, a GPU 1320, a RAM 1330, a ROM 1340, and an external storage device 1350. In addition, a liquid crystal display 1410 as the display device 1400 and a mouse 1510 and a keyboard 1520 as the input device 1500 are connected to the image processing apparatus 1300. Further, the image processing apparatus 1300 is connected to an image server 1210 as the storage device 1200 such as a picture archiving and communication system (PACS). Accordingly, image data can be stored in the image server 1210 or image data in the image server 1210 can be displayed on the liquid crystal display 1410.

Figure 3:
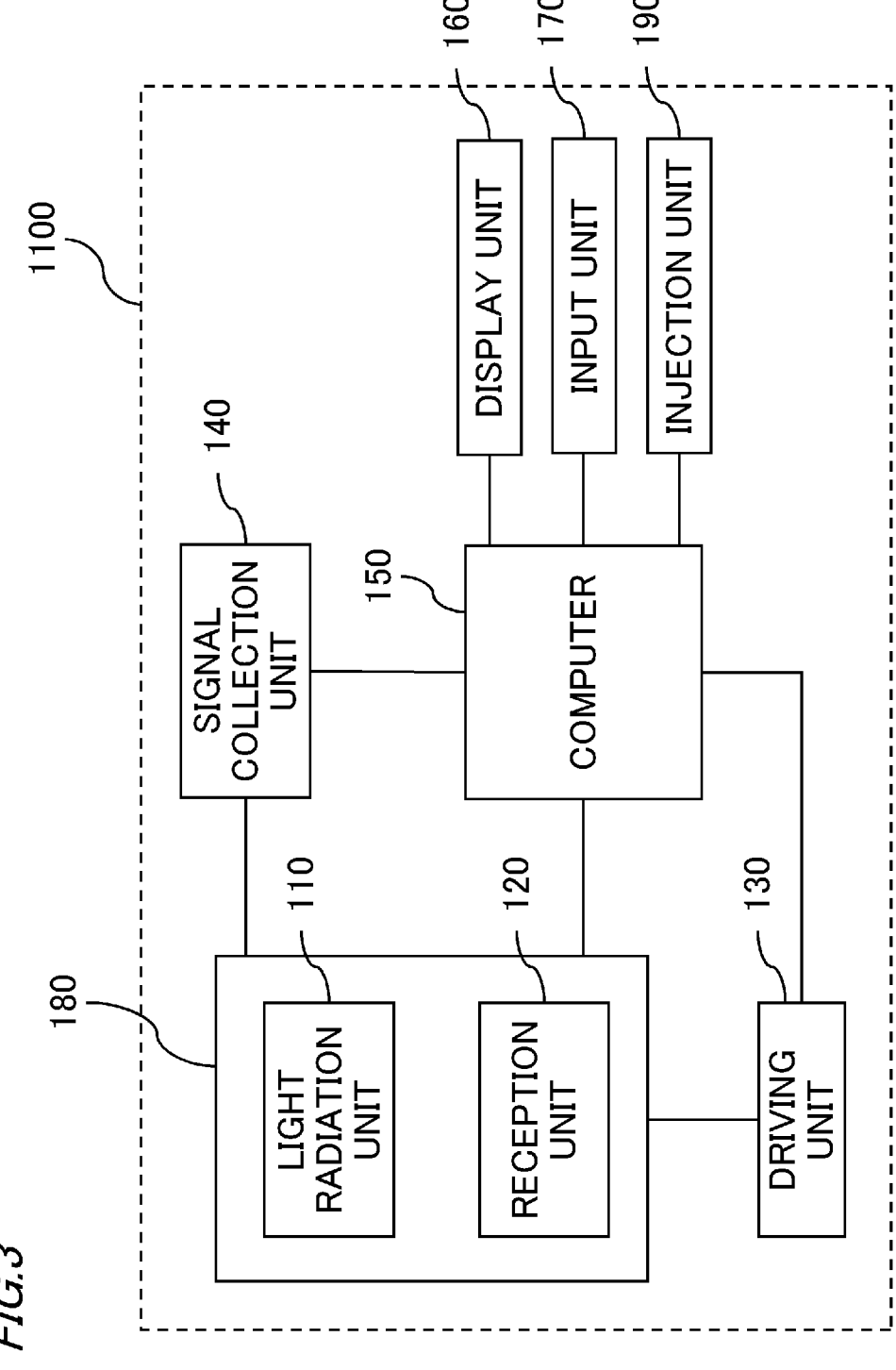
FIG. 3 is a detailed block diagram of a photoacoustic device according to an embodiment of the present invention.

Next, a configuration example of a device included in the system according to the present embodiment will be described. FIG. 3 is a schematic block diagram of a device included in the system according to the present embodiment.

Figure 4:
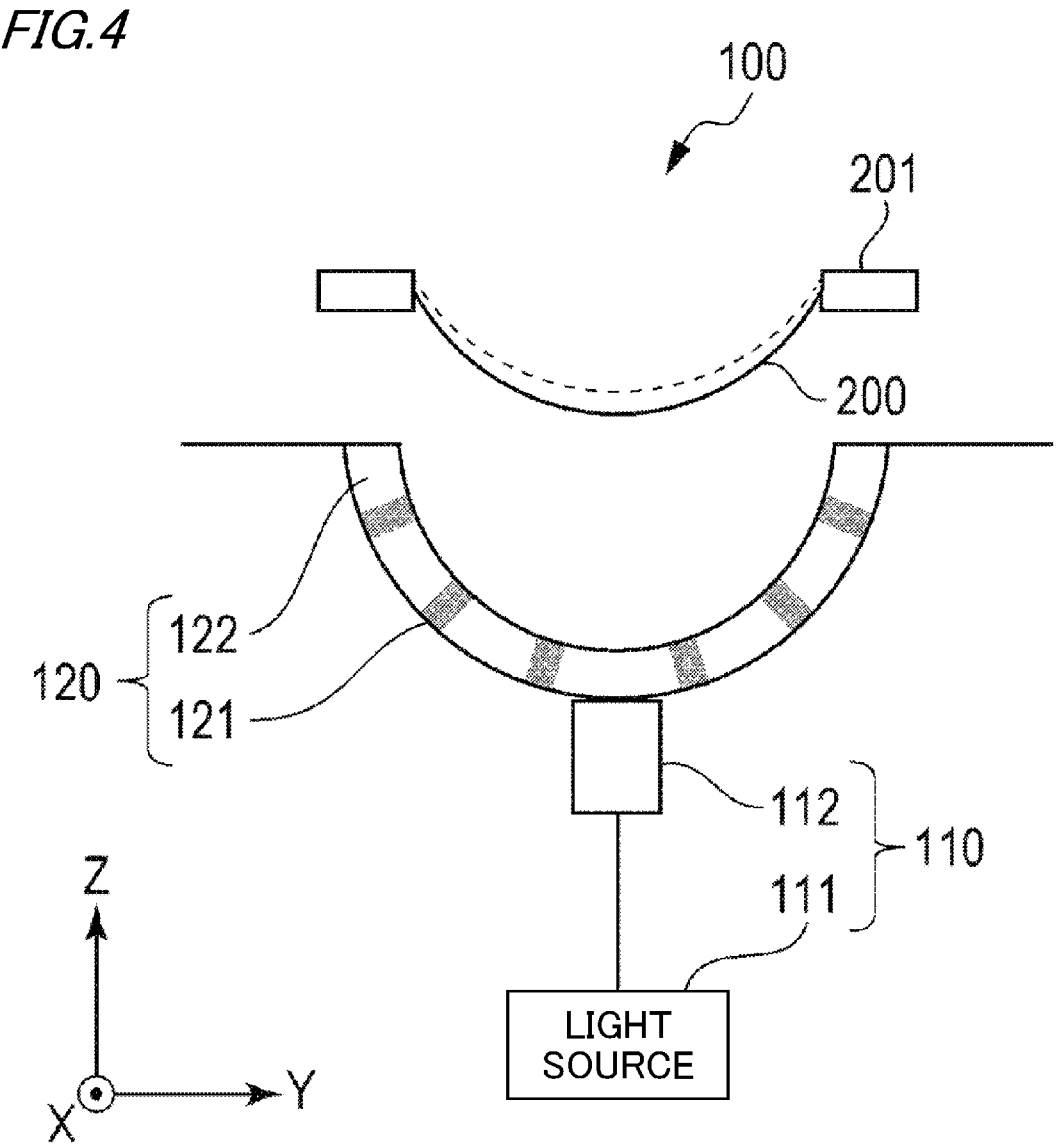
FIG. 4 is a schematic diagram of a probe according to an embodiment of the present invention.

The photoacoustic device 1100 according to the present embodiment includes a driving unit 130, a signal collection unit 140, the computer 150, a probe 180, and an injection unit 190. The probe 180 includes a light radiation unit 110 and a reception unit 120. FIG. 4 is a schematic diagram of the probe 180 according to the present embodiment. A measurement target is an object 100 into which a contrast agent has been injected by the injection unit 190. The driving unit 130 drives the light radiation unit 110 and the reception unit 120 to perform mechanical scanning. When the light radiation unit 110 radiates light to the object 100, acoustic waves are generated in the object 100. Acoustic waves generated according to photoacoustic effect caused by light are also called photoacoustic waves. The reception unit 120 outputs an electronic signal (photoacoustic signal) as an analog signal upon reception of the photoacoustic waves.

The signal collection unit 140 converts the analog signal output from the reception unit 120 into a digital signal and outputs the digital signal to the computer 150. The computer 150 stores the digital signal output from the signal collection unit 140 as signal data derived from the photoacoustic waves.

The computer 150 generates a photoacoustic image by performing signal processing on the stored digital signal. In addition, the computer 150 performs image processing on the obtained photoacoustic image and then outputs the photoacoustic image to the display unit 160. The display unit 160 displays an image based on the photoacoustic image. The displayed image is stored in a memory in the computer 150 or the storage device 1200 such as a data management system connected to a modality through a network on the basis of a storage instruction from a user or the computer 150.

In addition, the computer 150 also performs driving control of components included in the photoacoustic device. Furthermore, the display unit 160 may display a GUI and the like in addition to the image generated by the computer 150. The input unit 170 is configured such that a user can input information thereto. The user can perform operations such as instructions of starting or ending of measurement and storage of a generated image using the input unit 170.

Hereinafter, each component of the photoacoustic device 1100 according to the present embodiment will be described in detail.

(Light Radiation Unit 110)

The light radiation unit 110 includes a light source 111 that emits light and an optical system 112 that guides light projected from the light source 111 to the object 100. Meanwhile, light includes pulsed light such as so-called rectangular waves and triangular waves.

It is desirable that a pulse width of light emitted from the light source 111 be not more than 100 ns in consideration of heat containment conditions and stress containment conditions. In addition, a wavelength in a range of about 400 nm to 1600 nm may be used as a wavelength of light. When blood vessels are imaged in high resolution, a wavelength (at least 400 nm and not more than 700 nm) greatly absorbed in blood vessels may be used. When a deep part of a living body is imaged, light with a wavelength (at least 700 nm and not more than 1100 nm) typically less absorbed in background tissues (water, fat, and the like) of the living body may be used.

A laser or a light-emitting diode can be used as the light source 111. In addition, when measurement is performed using lights having a plurality of wavelengths, a light source that can change wavelengths may be used. Meanwhile, in a case where a plurality of wavelengths are radiated to an object, a plurality of light sources that generate lights having different wavelengths may be provided and lights may be alternately radiated from the light sources. In a case where a plurality of light sources are used, the light sources are integrally represented as a light source. As a laser, various lasers such as a solid laser, a gas laser, a dye laser, and a semiconductor layer can be used. For example, a pulsed laser such as a Nd:YAG laser or an alexandrite laser may be used as a light source. In addition, a Ti:sa laser or an optical parametric oscillators (OPO) laser that uses Nd:YAG laser light as excitation light may be used as a light source. Further, a flashlamp or a light-emitting diode may be used as the light source 111. In addition, a microwave source may be used as the light source 111.

Optical elements such as a lens, a mirror, and an optical fiber can be used for the optical system 112. In a case where a breast or the like is used as an object 100, a light projecting part of the optical system may be configured as a diffuser or the like which diffuses light in order to extend a beam diameter of pulsed light and radiate the pulsed light. On the other hand, in a photoacoustic microscope, the light projecting part of the optical system 112 may be configured as a lens or the like and a beam is focused and radiated in order to improve the resolution.

Meanwhile, the light radiation unit 110 may directly radiate light from the light source 111 to the object 100 without including the optical system 112.

(Reception Unit 120)

The reception unit 120 includes transducers 121 that output electronic signals upon reception of acoustic waves, and a support 122 that supports the transducers 121. In addition, the transducers 121 may be transmission means that transmit acoustic waves. A transducer as reception means and a transducer as transmission means may be a single (common) transducer or separate components.

As a member constituting the transducers 121, a ceramic material represented by lead zirconate titanate (PZT), a polymer piezoelectric film material represented by polyvinylidene fluoride (PVDF), and the like can be used. In addition, an element other than a piezoelectric element may be used. For example, transducers using capacitive micromachined ultrasonic transducers (CMUT) and the like can be used. Meanwhile, any transducer may be employed as long as it can output an electronic signal upon reception of acoustic waves. In addition, a signal acquired by a transducer is a time-resolved signal. That is, the amplitude of a signal acquired by a transducer represents a value based on a sound pressure (e.g., a value proportional to a sound pressure) received through the transducer at each time.

Frequency components constituting a photoacoustic wave are typically 100 KHz to 100 MHz, and a transducer capable of detecting these frequencies may be employed as the transducers 121.

The support 122 may be formed of a metal material having high mechanical strength. Mirror finishing or processing for light scattering may be performed on the surface of the support 122 on the side of the object 100 such that a large quantity of radiated light is input to the object. In the present embodiment, the support 122 has a hemispherical enclosure shape and is configured to be able to support a plurality of transducers 121 on a hemispherical enclosure. In this case, directional axes of the transducers 121 disposed in the support 122 converge on the vicinity of the center of curvature of the hemisphere. Then, picture quality in the vicinity of the center of curvature increases when imaging is performed using signals output from the plurality of transducers 121. Meanwhile, the support 122 may employ any configuration as long as it can support the transducers 121. The support 122 may be configured such that a plurality of transducers are arranged side by side on a plane or a curved surface which is called a 1D array, a 1.5D array, a 1.75D array, or a 2D array. The plurality of transducers 121 correspond to a plurality of reception means.

In addition, the support 122 may serve as a container storing an acoustic matching material. That is, the support 122 may be used as a container for disposing the acoustic matching material between the transducers 121 and the object 100.

In addition, the reception unit 120 may include an amplifier that amplifies time-series analog signals output from the transducers 121. Further, the reception unit 120 may include an A/D converter that converts time-series analog signals output from the transducers 121 into time-series digital signals. That is, the reception unit 120 may include the signal collection unit 140 which will be described later.

The space between the reception unit 120 and the object 100 is filled with a medium capable of propagating photoacoustic waves. As this medium, a material that can propagate acoustic waves, allows matching of acoustic characteristics at the interface between the object 100 and the transducers 121, and has as high photoacoustic wave transmittance as possible is employed. For example, water, an ultrasonic gel, or the like can be employed as this medium.

FIG. 4 shows a side view of the probe 180. The probe 180 according to the present embodiment includes the reception unit 120 in which a plurality of transducers 121 are three-dimensionally arranged in the hemispherical support 122 having an opening. In addition, a light projection unit of the optical system 112 is disposed at the bottom of the support 122.

In the present embodiment, the shape of the object 100 is held when the object 100 comes into contact with a holder 200, as illustrated in FIG. 4.

The space between the reception unit 120 and the holder 200 is filled with a medium capable of propagating photoacoustic waves. As this medium, a material that can propagate acoustic waves, allows matching of acoustic characteristics at the interface between the object 100 and the transducers 121, and has as high photoacoustic wave transmittance as possible is employed. For example, water, an ultrasonic gel, or the like can be employed as this medium.

The holder 200 as holding means is used to hold the shape of the object 100 during measurement. It is possible to curb movement of the object 100 and keep the position of the object 100 within the holder 200 by holding the object 100 by the holder 200. As a material of the holder 200, a resin material such as polycarbonate, polyethylene, or polyethylene terephthalate can be used.

The holder 200 is attached to a mounting part 201. The mounting part 201 may be configured such that a plurality of types of holders 200 can be exchanged in accordance with the size of an object. For example, the mounting part 201 may be configured such that holders having different radiuses of curvature and different centers of curvature can be exchanged.

(Driving Unit 130)

The driving unit 130 is a part that changes relative positions of the object 100 and the reception unit 120. The driving unit 130 includes a motor such as a stepping motor for generating a driving force, a driving mechanism for delivering the driving force, and a position sensor for detecting position information of the reception unit 120. As the driving mechanism, a lead screw mechanism, a link mechanism, a gear mechanism, a hydraulic mechanism, or the like can be used. In addition, as the position sensor, a potentiometer using an encoder, a variable resistor, a linear scale, a magnetic sensor, an infrared sensor, an ultrasonic sensor, or the like, or the like can be used.

Meanwhile, the relative positions of the object 100 and the reception unit 120 changed by the driving unit 130 are not limited according to XY directions (two dimensions) and may be changed in one dimension or three dimensions.

Meanwhile, the driving unit 130 may fix the reception unit 120 and move the object 100 as long as it can change the relative positions of the object 100 and the reception unit 120. In a case where the object 100 is moved, a configuration in which the object 100 is moved by moving the holder that holds the object 100, or the like is conceivable. In addition, both the object 100 and the reception unit 120 may be moved.

The driving unit 130 may move the relative positions continuously or in a step-and-repeat manner. The driving unit 130 may be an electromotive stage that allows movement along a programmed trajectory or a manual stage.

In addition, although the driving unit 130 performs scanning by simultaneously driving the light radiation unit 110 and the reception unit 120 in the present embodiment, the driving unit 130 may drive only the light radiation unit 110 or only the reception unit 120.

Meanwhile, in a case where the probe 180 is of hand-held type equipped with a gripping part, the photoacoustic device 1100 may not include the driving unit 130.

(Signal Collection Unit 140)

The signal collection unit 140 includes an amplifier that amplifies electronic signals that are analog signals output from the transducers 121, and an A/D converter that converts the analog signals output from the amplifier into digital signals. The digital signals output from the signal collection unit 140 are stored in the computer 150. The signal collection unit 140 is also called a data acquisition system (DAS). An electronic signal in the present specification is a concept including both an analog signal and a digital signal. Meanwhile, a light detection sensor such as a photodiode may detect light projection from the light radiation unit 110 and the signal collection unit 140 may start the aforementioned processing by synchronizing this detection result with a trigger.

(Computer 150)

The computer 150 as an information processing device is configured as hardware like the image processing apparatus 1300. That is, units that execute an arithmetic operation function of the computer 150 can be composed of a processor such as a CPU or a graphics processing unit (GPU), and an arithmetic operation circuit such as a field programmable gate array (FPGA). These units may be composed of not only a single processor and a single arithmetic operation circuit but also a plurality of processors and a plurality of arithmetic operation circuits.

A unit that executes a storage function of the computer 150 may be a volatile medium such as a random access memory (RAM). Meanwhile, a storage medium in which programs are stored is a non-transient storage medium. Further, the unit that executes the storage function of the computer 150 may be configured as not only a single storage medium but also a plurality of storage media.

A unit that executes a control function of the computer 150 is configured as an arithmetic operation element such as a CPU. The unit that executes the control function of the computer 150 controls the operation of each component of the photoacoustic device. The unit that executes the control function of the computer 150 may receive instruction signals according to various operations such as starting of measurement from the input unit 170 and control each component of the photoacoustic device. In addition, the unit that executes the control function of the computer 150 may read program code stored in the unit that executes the storage function and control the operation of each component of the photoacoustic device. That is, the computer 150 can serve as a control device of the system according to the present embodiment.

Meanwhile, the computer 150 and the image processing apparatus 1300 may be configured as the same hardware. A single piece of hardware may execute the functions of both the computer 150 and the image processing apparatus 1300. That is, the computer 150 may execute the function of the image processing apparatus 1300. Further, the image processing apparatus 1300 may execute the function of the computer 150 as an information processing device.

(Display Unit 160)

The display unit 160 is a display such as a liquid crystal display or an organic electroluminescence (EL) device. In addition, the display unit 160 may display a GUI for operating images or devices.

Meanwhile, the display unit 160 and the display device 1400 may be the same display. That is, a single display can execute the functions of both the display unit 160 and the display device 1400.

(Input Unit 170)

As the input unit 170, an operation console composed of a mouse, a keyboard, and the like that can be operated by a user can be employed. In addition, the display unit 160 may be configured as a touch panel and the display unit 160 may be used as the input unit 170.

Meanwhile, the input unit 170 and the input device 1500 may be the same device. That is, a single device may execute the functions of both the input unit 170 and the input device 1500.

(Injection Unit 190)

The injection unit 190 is configured such that a contrast agent can be injected into the object 100 from the outside of the object 100. For example, the injection unit 190 can include a contrast agent container and an injection needle sticking into an object. However, the injection unit 190 is not limited thereto and various types are applicable as long as they can inject a contrast agent into the object 100. In this case, the injection unit 190 may be a known injection system or injector, for example. Meanwhile, the computer 150 as a control device may inject a contrast agent into the object 100 by controlling the operation of the injection unit 190. In addition, a user may inject a contrast agent into the object 100 by operating the injection unit 190.

(Object 100)

Although the object 100 does not constitute the system, it will be described below. The system according to the present embodiment can be used for the purpose of diagnosis of malignant tumor, a vascular disease, or the like of people or animals, observation of the progress of chemical treatment, and the like. Accordingly, as the object 100, a target part of diagnosis such as a living body, specifically, the breast, each organ, the vasoganglion, the head, the neck, the abdomen, the limbs including fingers or toes, or the like of a human body or an animal may be conceived. For example, if a human body is a measurement target, oxyhemoglobin or deoxyhemoglobin, blood vessels containing a large amount of these substances, new blood vessels formed near tumor, or the like may be used as a target of a light absorber. In addition, a plaque of the carotid artery wall or the like may be used as a target of the light absorber. In addition, melanin, collagen, lipoid, and the like included in the skin may be used as a target of the light absorber. Further, a contrast agent injected into the object 100 can be used as a light absorber. As a contrast agent used for photoacoustic imaging, a pigment such as indocyanine green (ICG) or methylene blue (MB), gold particles, a mixture thereof, or a material obtained by integrating or chemically modifying these materials and introduced from the outside may be used. In addition, a phantom that imitating a living body may be used as the object 100.

Meanwhile, components of the photoacoustic device may be configured as separate devices or configured as an integrated single device. In addition, at least some components of the photoacoustic device may be configured as a single device in one body.

Meanwhile, devices constituting the system according to the present embodiment may be configured as separate pieces of hardware or all the devices may be configured as a single piece of hardware. The functions of the system according to the present embodiment may be configured using any hardware.

Figure 5:
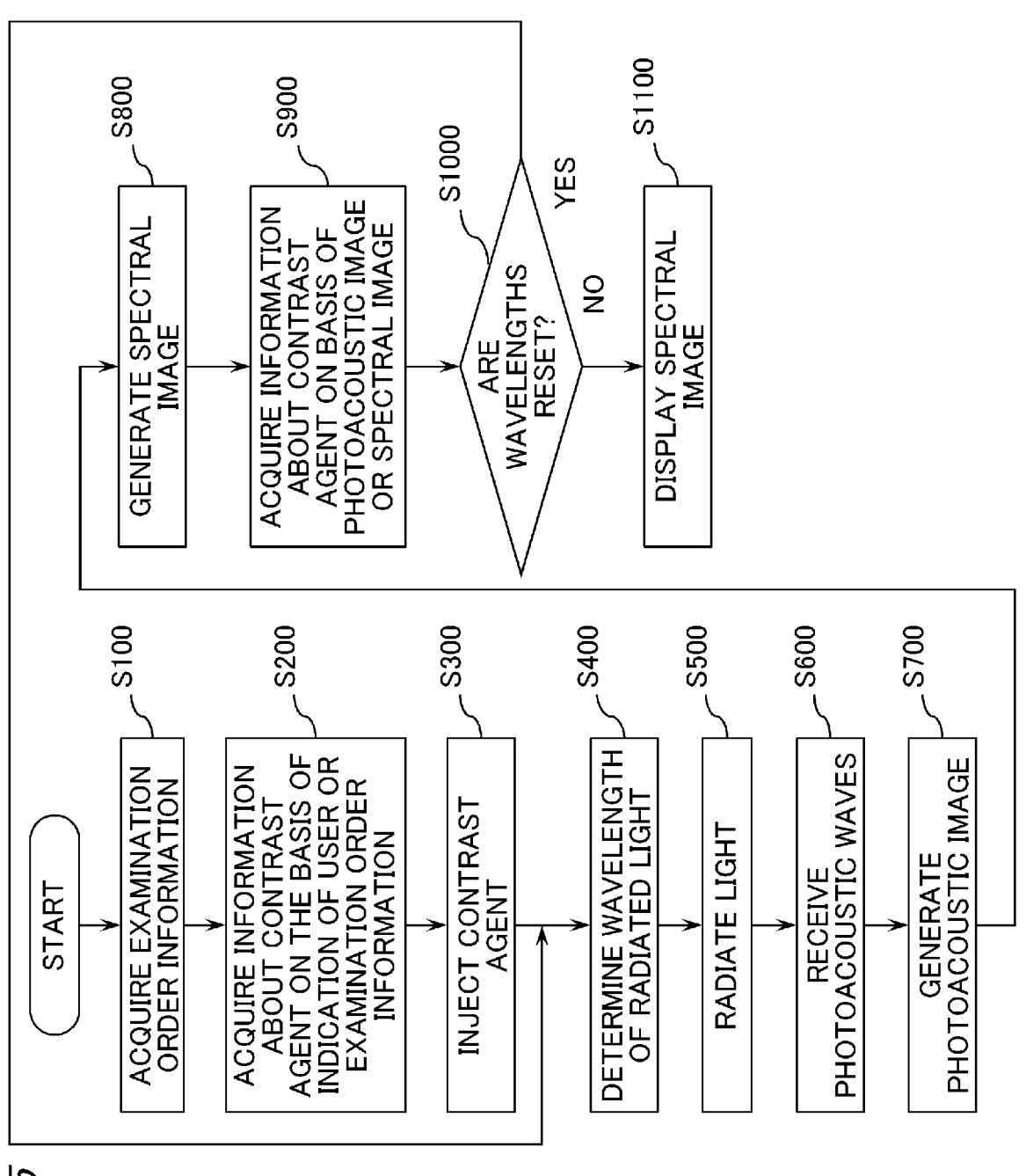
FIG. 5 is a flowchart of an image processing method according to an embodiment of the present invention.

Next, an image generation method according to the present embodiment will be described using a flowchart illustrated in FIG. 5. Meanwhile, the flowchart illustrated in FIG. 5 includes processes representing the operation of the system according to the present embodiment and processes representing an operation of a user such as a doctor.

(S100: Process of Acquiring Examination Order Information)

The computer 150 of the photoacoustic device 1100 acquires examination order information transmitted from an in-hospital information system such as a hospital information system (HIS) or a radiology information system (RIS). The examination order information includes information such as a modality type used for an examination and a contrast agent to be used for the examination.

(S200: Process of Acquiring Information about Contrast Agent on the Basis of Instruction of User or Examination Order Information)

The computer 150 as contrast agent information acquisition means acquires information about a contrast agent. The user may indicate a type and a concentration of a contrast agent to be used for the examination using the input unit 170. In this case, the computer 150 can acquire the information about the contrast agent through the input unit 170. In addition, in a case where the examination order information acquired in S100 includes the information about the contrast agent, the computer 150 may acquire the information about the contrast agent by reading the information about the contrast agent from the examination order information. The computer 150 may acquire the information about the contrast agent on the basis of at least one of instruction of the user and the examination order information. For example, as information about the contrast agent which represents conditions of the contrast agents, a type of the contrast agent, a concentration of the contrast agent, and the like are conceivable.

Figure 10:
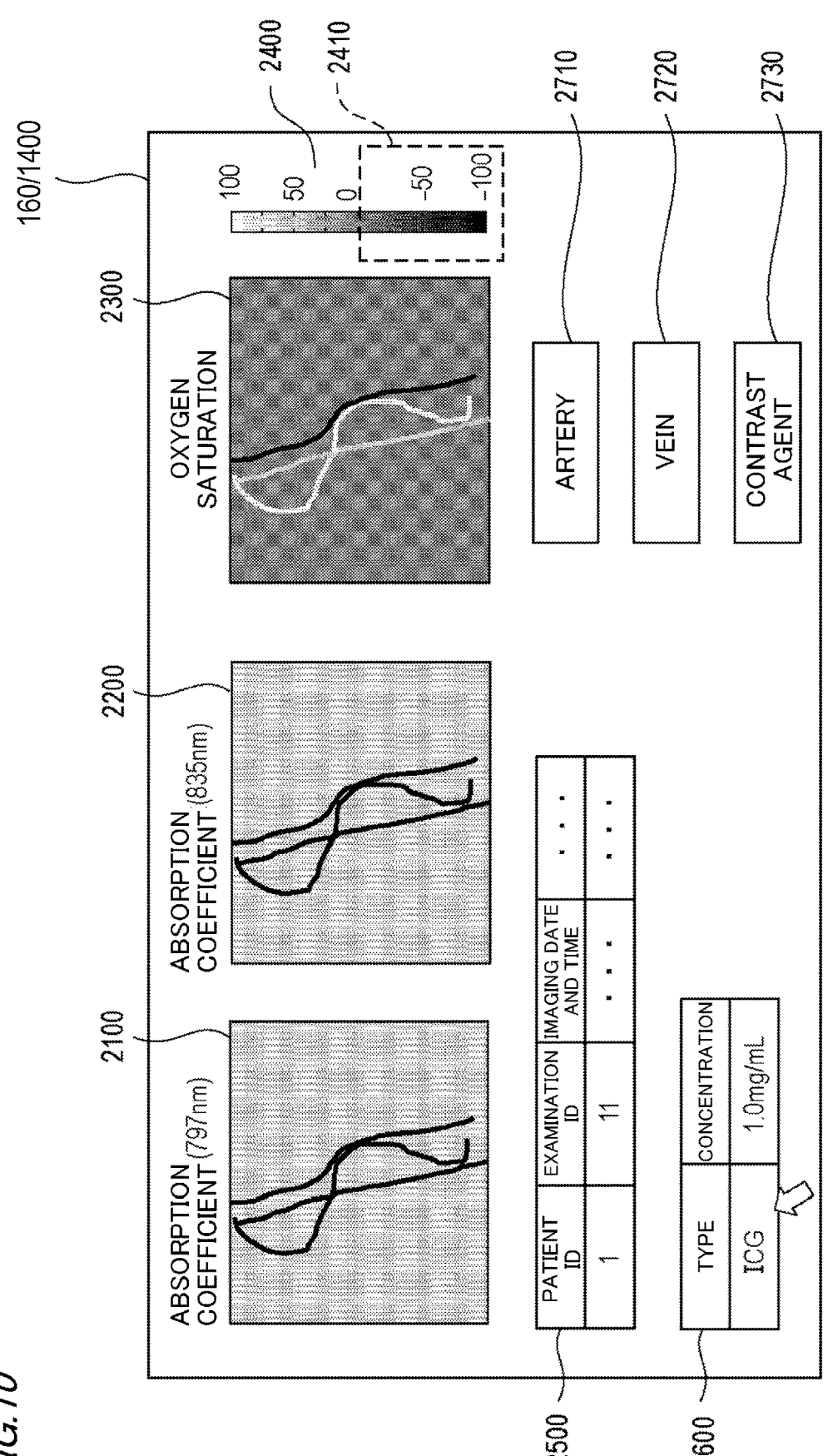
FIG. 10 is a diagram illustrating a GUI according to an embodiment of the present invention.

FIG. 10 illustrates an example of a GUI displayed on the display unit 160. An item 2500 of the GUI displays examination order information such as a patient ID, an examination ID, and an imaging date and time. The item 2500 may include a display function of displaying examination order information acquired from an external device such as an HIS or an RIS and an input function of allowing a user to be able to input examination order information using the input unit 170. An item 2600 of the GUI displays information about a contrast agent such as a type of the contrast agent and a concentration of the contrast agent. The item 2600 may include a display function of displaying information about a contrast agent acquired from an external device such as an HIS or an MS and an input function of allowing a user to be able to input information about a contrast agent using the input unit 170. In the item 2600, information about a contrast agent such as a type and a concentration of the contrast agent may be input among a plurality of choices through a method such as a pull-down. Meanwhile, the GUI illustrated in FIG. 10 may be displayed on the display device 1400.

Meanwhile, in a case where the image processing apparatus 1300 has not received an input instruction for the information about a contrast agent from the user, information about a contrast agent set as a default from among a plurality of pieces of information about contrast agents may be acquired. In the case of the present embodiment, a case in which ICG is set as a default contrast agent type and 1.0 mg/mL is set as a default contrast agent concentration is described. Although a type and a concentration of a contrast agent set as default are displayed in the item 2600 of the GUI in the present embodiment, information about a contrast agent may not be set as default. In this case, information about a contrast agent may not be displayed in the item 2600 of the GUI on an initial screen.

(S300: Process of Injecting Contrast Agent)

The injection unit 190 injects the contrast agent into the object. When the user has injected the contrast agent into the object using the injection unit 190, the user may transmit a signal representing that the contrast agent has been injected from the input unit 170 to the computer 150 as a control device by operating the input unit 170. In addition, the injection unit 190 may transmit a signal representing that the contrast agent has been injected into the object 100 to the computer 150. Meanwhile, the contrast agent may be put into the object without using the injection unit 190. For example, the contrast agent may be put into a living body as an object in such a manner that the living body inhales the sprayed contrast agent.

S400 which will be described later may be executed after a time for the contrast agent to spread to a contrasting target in the object 100 after injection of the contrast agent.

(S400: Process of Determining Wavelength of Radiated Light)

The computer 150 as wavelength determination means determines a wavelength of radiated light on the basis of the information about the contrast agent acquired in S200. In the present embodiment, the computer 150 determines a plurality of wavelengths on the basis of the information about the contrast agent in order to generate a spectral image. Hereinafter, a combination of wavelengths for easily identifying a region corresponding to the contrast agent in a spectral image will be described.

In the present embodiment, a case in which an image according to formula (1) is generated as a spectral image in S800 which will be described later is conceived. According to formula (1), image values in response to an actual oxygen saturation are calculated with respect to an area of blood vessels in the spectral image. However, image values considerably change depending on a used wavelength with respect to the area of the contrast agent in the spectral image. Furthermore, the image values also considerably change depending on the absorption coefficient spectrum of the contrast agent with respect to the area of the contrast agent in the spectral image. As a result, there are cases in which image values of the area of the contrast agent in the spectral image become values that cannot be distinguished from the image values of the area of the blood vessels. Meanwhile, to ascertain a three-dimensional distribution of the contrast agent, it is desirable that the image values of the area of the contrast agent in the spectral image be values that can be distinguished from the image values of the area of the blood vessels.

Accordingly, the inventor conceived a method of controlling image values of a contrast agent in a spectral image by adaptively changing a wavelength of radiated light according to conditions of the contrast agent used for an examination. That is, the inventor devised a method by which an information processing device determines a wavelength of radiated light which allows an area of a contrast agent in a spectral image to be able to be distinguished from an area of blood vessels on the basis of information about contrast agent.

Specifically, in a case in which an image using formula (1) is generated as a spectral image, a wavelength of radiated light may be determined using the fact that the oxygen saturation of the arteriovenous falls within about a range of 60% to 100% in percent indication. That is, the computer 150 as an information processing device may determine two wavelengths such that a value of formula (1) corresponding to the contrast agent in the spectral image becomes less than 60% or greater than 100% on the basis of the information about the contrast agent. In addition, the computer 150 may determine two wavelengths such that a sign of image values of an area corresponding to the contrast agent in the spectral image becomes reverse to a sign of image values of other areas on the basis of the information about the contrast agent.

Figure 6:
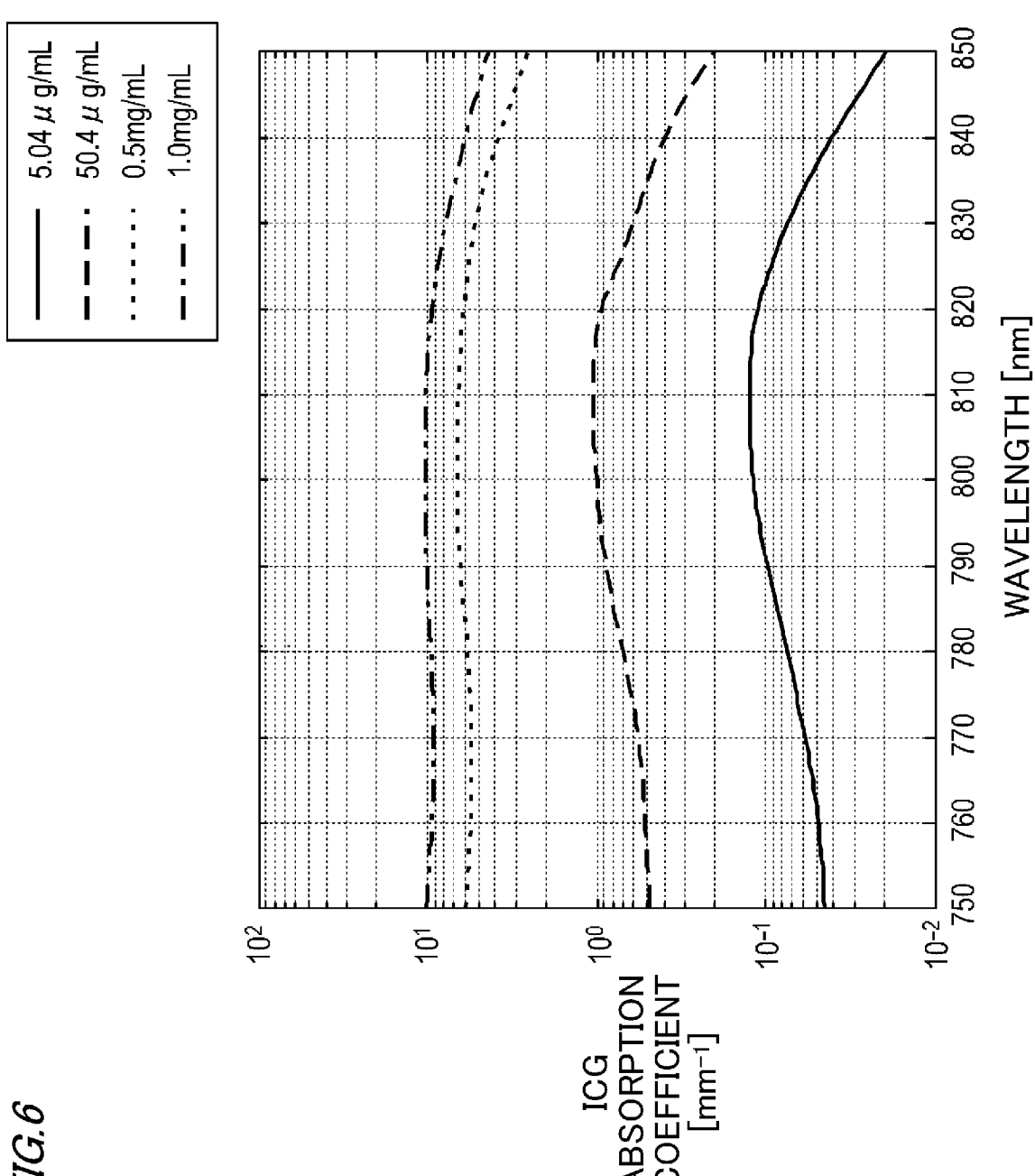
FIG. 6 is a graph showing an absorption coefficient spectrum when an ICG concentration has been changed.
Figures 7A, 7B, 7C, 7D:
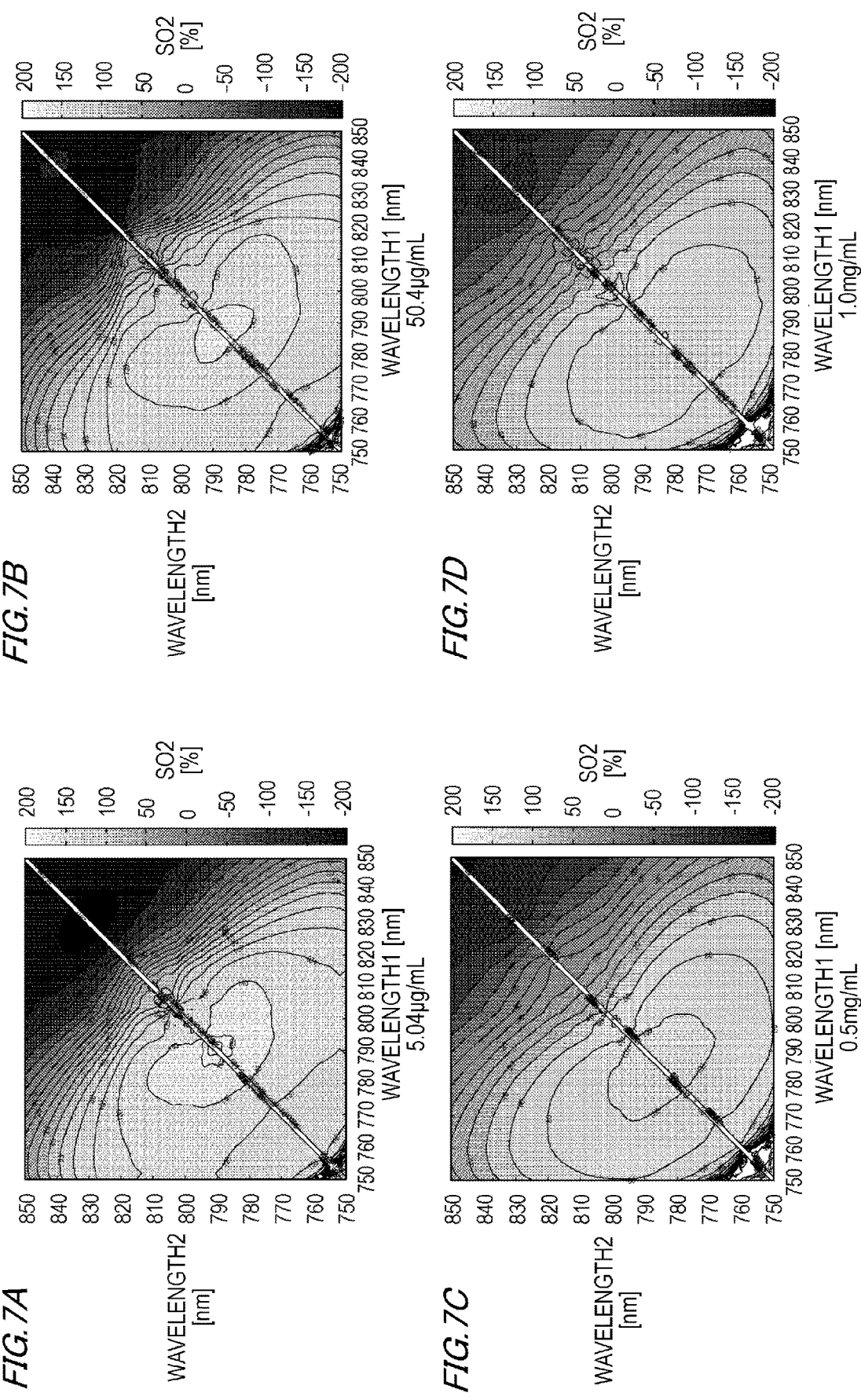
FIG. 7A to FIG. 7D are contour graphs of calculation values of formula (1) corresponding to a contrast agent when wavelength combinations have been changed.

Next, change in image values corresponding to a contrast agent when the concentration of the contrast agent as information about the contrast agent has been changed will be described. FIG. 6 is a spectrum diagram illustrating change in an absorption coefficient spectrum when the concentration of ICG as a contrast agent has been changed. FIG. 6 illustrates spectra in a case where the concentration of ICG is 5.04 µg/mL, 50.4 µg/mL, 0.5 mg/mL, and 1.0 mg/mL from the bottom. As illustrated in FIG. 6, it is understood that a degree of absorption of light increases as the concentration of the contrast agent increases. In addition, it is understood that image values corresponding to the contrast agent in a spectral image change in response to the concentration of the contrast agent because a ratio of absorption coefficients corresponding to two wavelengths changes in response to the concentration of the contrast agent. A ratio of absorption coefficients corresponding to two wavelengths also changes when the type of the contrast agent has changed as in a case where the concentration of the contrast agent has changed. Accordingly, it is understood that image values corresponding to the contrast agent in a spectral image also change in response to the type of the contrast agent.

Here, a spectral image obtained by imaging a living body into which ICG has been injected using the photoacoustic device will be described. FIG. 11A to FIG. 13B illustrate spectral images obtained through imaging when ICG has been injected with concentrations changed. In all imaging operations, ICG has been injected by 0.1 mL under the skin or into the skin of a hand or a foot. ICG injected under the skin or into the skin is selectively taken into lymphatic vessels, and thus lumens of the lymphatic vessels are contrasted. In addition, in all imaging operations, imaging has been performed within 5 minutes to 60 minutes from injection of ICG. Furthermore, all spectral images are spectral images generated from photoacoustic images obtained by radiating light with a wavelength of 797 nm and light with a wavelength of 835 nm to the living body.

Figure 11B:
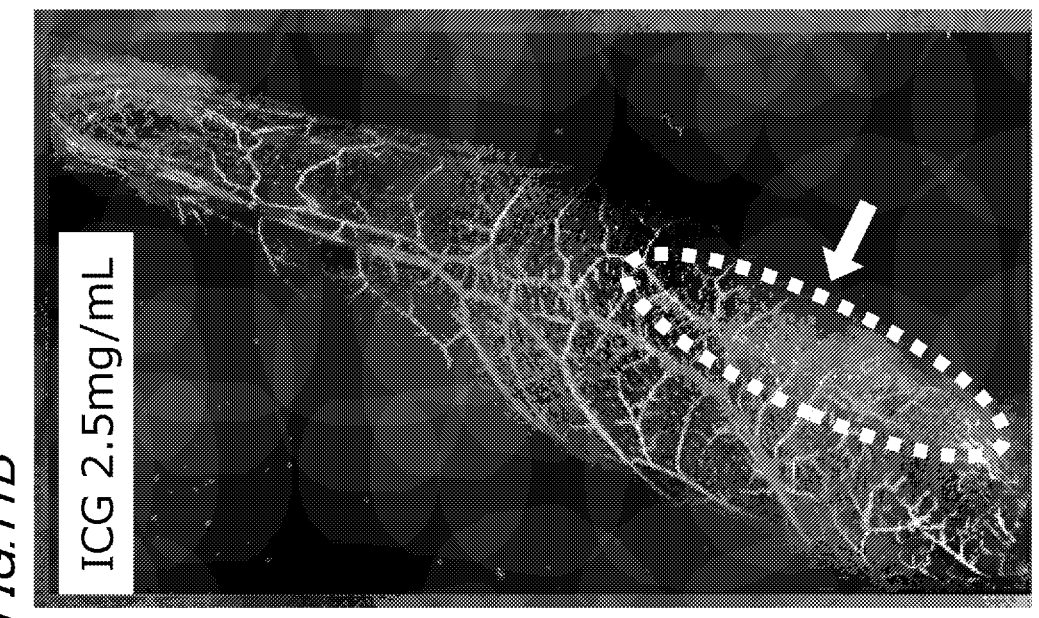
FIG. 11A and FIG. 11B are spectral images of a right forearm extensor when an ICG concentration has been changed.
Figure 11A:
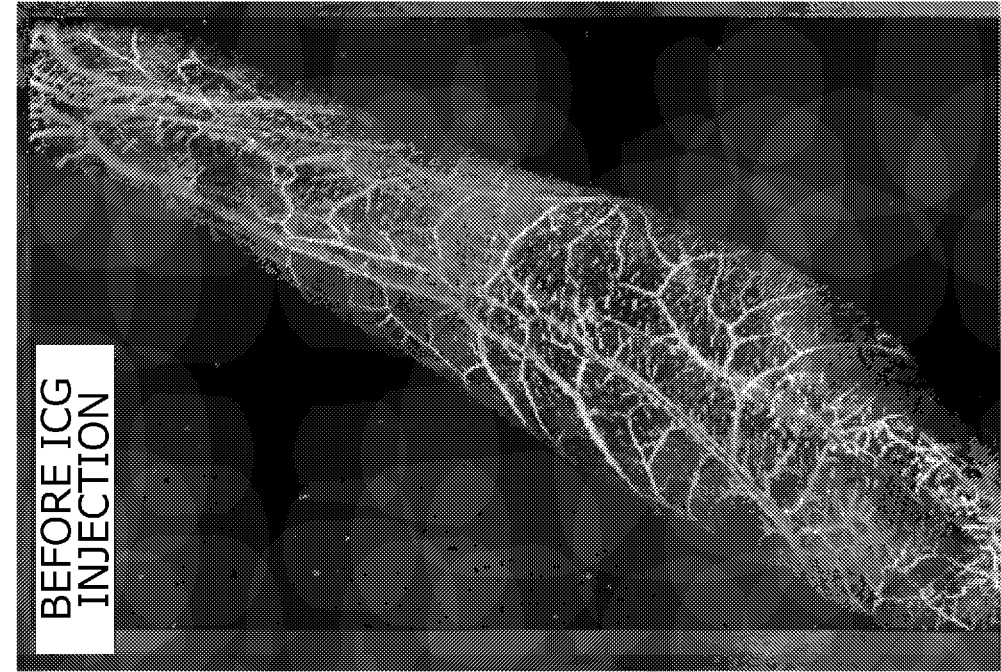

FIG. 11A illustrates a spectral image of a right forearm extensor when ICG has not been injected. On the other hand, FIG. 11B illustrates a spectral image of the right forearm extensor when ICG has been injected in a concentration of 2.5 mg/mL. Lymphatic vessels are drawn in an area indicated by a dotted line and an arrow in FIG. 11B.

Figure 12B:
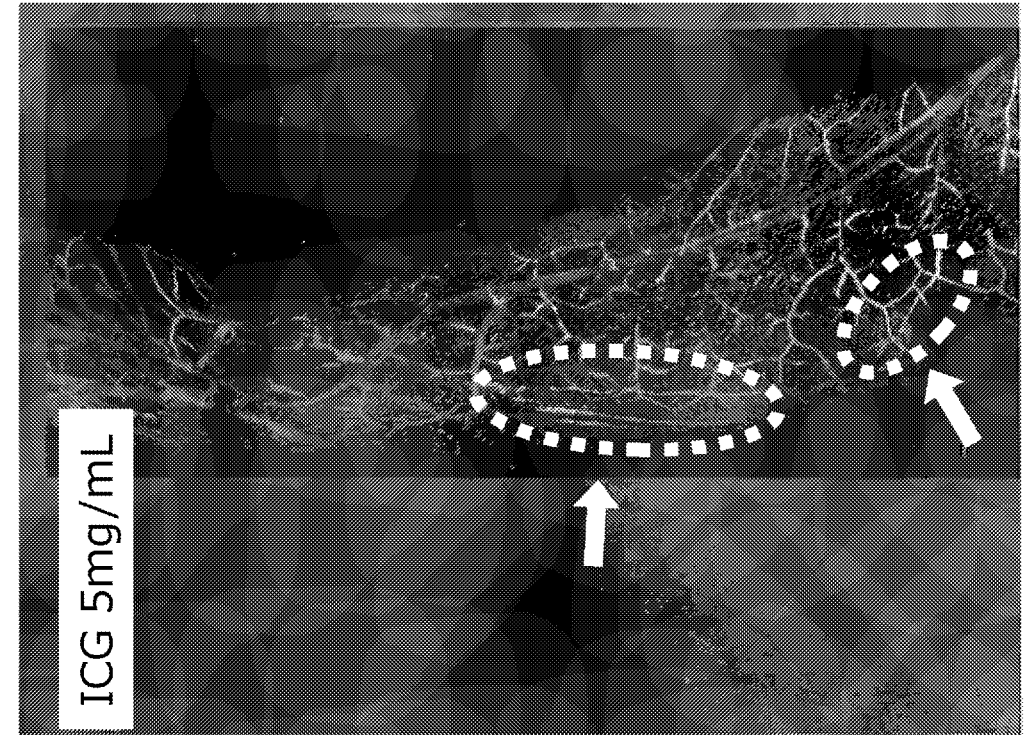
FIG. 12A and FIG. 12B are spectral images of a left forearm extensor when an ICG concentration has been changed.
Figure 12A:
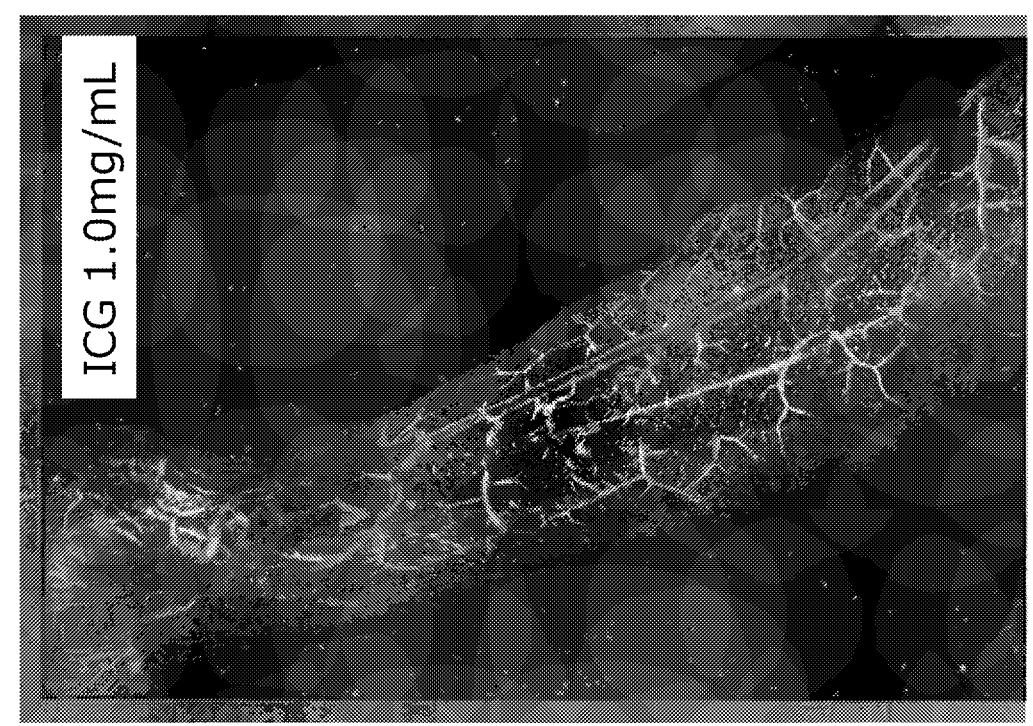

FIG. 12A illustrates a spectral image of a left forearm extensor when ICG has been injected in a concentration of 1.0 mg/mL. FIG. 12B illustrates a spectral image of the left forearm extensor when ICG has been injected in a concentration of 5.0 mg/mL. Lymphatic vessels are drawn in areas indicated by dotted lines and arrows in FIG. 12B.

Figure 13B:
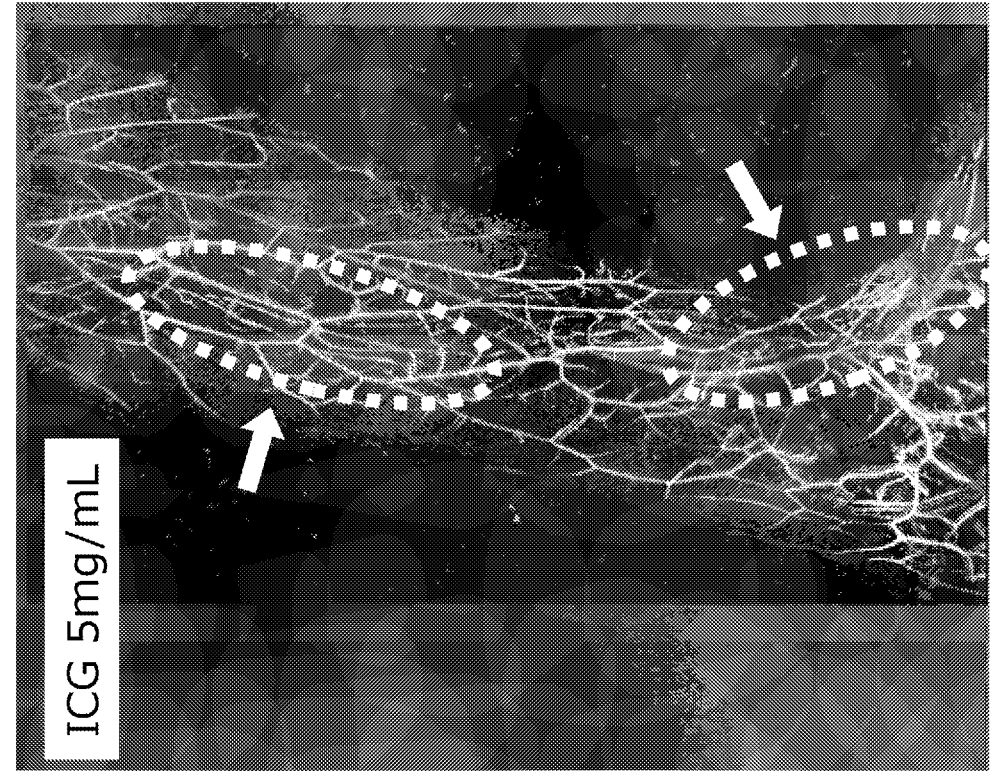
FIG. 13A and FIG. 13B are spectral images of the inside of a right lower leg and the inside of a left lower leg when an ICG concentration has been changed.
Figure 13A:
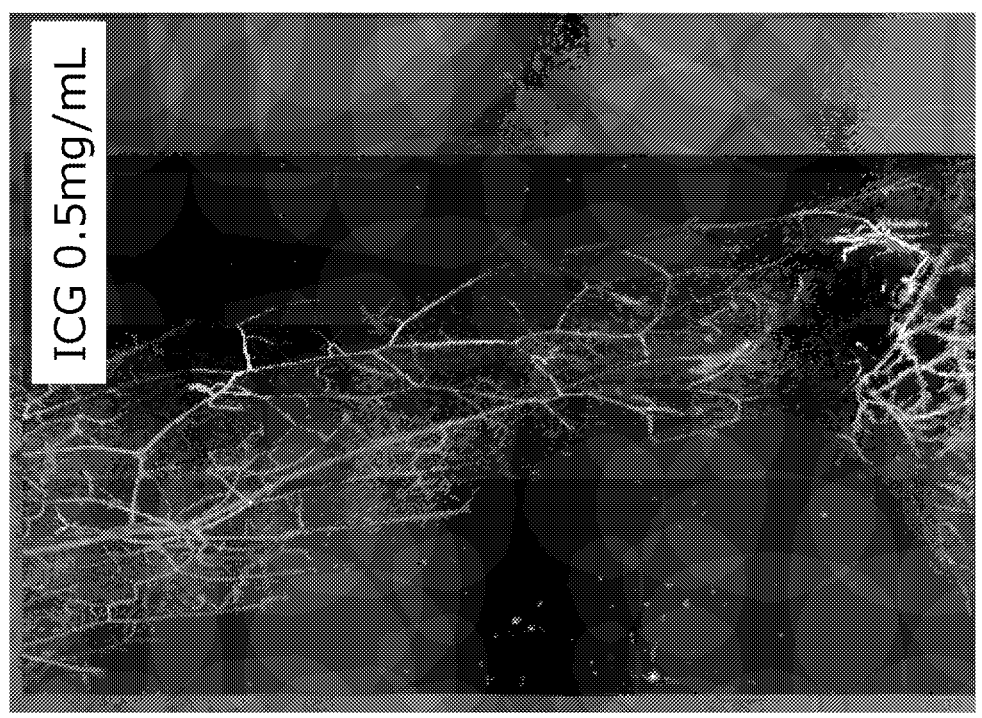

FIG. 13A illustrates a spectral image of the inside of a right lower leg when ICG has been injected in a concentration of 0.5 mg/mL. FIG. 13B illustrates a spectral image of the inside of the left lower leg when ICG has been injected in a concentration of 5.0 mg/mL. Lymphatic vessels are drawn in areas indicated by dotted lines and arrows in FIG. 13B.

According to the spectral images illustrated in FIG. 11A to FIG. 13B, it is understood that visibility of lymphatic vessels in the spectral images is improved as the concentration of ICG increases. In addition, according to FIG. 11A to FIG. 13B, it is understood that lymphatic vessels can be satisfactorily drawn in a case where the concentration of ICG is at least 2.5 mg/mL. That is, it is possible to clearly visually recognize lymphatic vessels on lines in a case where the concentration of ICG is at least 2.5 mg/mL. Accordingly, in a case where ICG is used as a contrast agent, the concentration thereof may be at least 2.5 mg/mL. Meanwhile, the concentration of ICG may be greater than 5.0 mg/mL in consideration of dilution of ICG in a living body. However, when the solubility of diagnogreen is taken into account, it is difficult to melt it in an aqueous solution in a concentration of at least 10.0 mg/mL.

As described above, a concentration of ICG injected to a living body may be at least 2.5 mg/mL and not more than 10.0 mg/mL and, preferably, at least 5.0 mg/mL and not more than 10.0 mg/mL.

Accordingly, the computer 150 may be configured to selectively receive an instruction from a user which indicates an ICG concentration within the aforementioned numerical value range in a case where ICG is input as a contrast agent type in the item 2600 of GUI illustrated in FIG. 10. That is, in this case, the computer 150 may be configured such that it does not receive an instruction from a user which indicates an ICG concentration that does not fall within the aforementioned numerical value range. Accordingly, the computer 150 may be configured such that it does not receive an instruction from a user which indicates an ICG concentration less than 2.5 mg/mL or greater than 10.0 mg/mL in a case where information representing that a contrast agent type is ICG is acquired. In addition, the computer 150 may be configured such that it does not receive an instruction from a user which indicates an ICG concentration less than 5.0 mg/mL or greater than 10.0 mg/mL in a case where information representing that a contrast agent type is ICG is acquired.

The computer 150 may configure a GUI such that a user cannot indicate an ICG concentration that does not fall within the aforementioned numerical value range on the GUI. That is, the computer 150 may cause the GUI to be displayed such that a user cannot indicate an ICG concentration that does not fall within the aforementioned numerical value range on the GUI. For example, the computer 150 may cause a pull-down through which an ICG concentration within the aforementioned numerical value range can be selectively indicated to be displayed on the GUI. The computer 150 may configure a GUI such that an ICG concentration that does not fall within the aforementioned numerical value range in the pull-down is displayed as gray out and the gray-out concentration cannot be selected.

In addition, the computer 150 may notify an alert when an ICG concentration that does not fall the aforementioned numerical value range has been indicated by a user on the GUI. As a notification method, any method such as display of an alert on the display unit 160, sound, and lighting of a lamp can be employed.

Furthermore, the computer 150 may cause the display unit 160 to display the aforementioned numerical value range as a concentration of ICG to be injected into an object when ICG has been selected as a contrast agent type on the GUI.

Meanwhile, a concentration of a contrast agent injected into an object is not limited to the numerical value range represented here and a suitable concentration according to a purpose can be used. In addition, although an example of a case in which a contrast agent type is ICG has been described here, the aforementioned configuration can be applied to other contrast agents in the same manner.

By configuring the GUI in this manner, it is possible to support a user injecting a suitable concentration of a contrast agent into an object depending on the type of a contrast agent scheduled to be injected into the object.

Next, change in image values corresponding to a contrast agent in a spectral image when a combination of wavelengths has changed will be described. FIG. 7A to FIG. 7D illustrate simulation results of image values (oxygen saturation values) corresponding to a contrast agent in spectral images in combinations of two wavelengths. Vertical axes and horizontal axes of FIG. 7A to FIG. 7D represent a first wavelength and a second wavelength. Isolines of image values corresponding to a contrast agent in spectral images are illustrated in FIG. 7A to FIG. 7D. FIG. 7A to FIG. 7D illustrate image values corresponding to the contrast agent in spectral images when an ICG concentration is 5.04 µg/mL, 50.4 µg/mL, 0.5 mg/mL, and 1.0 mg/mL, respectively. As illustrated in FIG. 7A to FIG. 7D, there are cases in which image values corresponding to the contrast agent in a spectral image become 60% to 100% depending on a selected combination of wavelengths. As described above, when such a wavelength combination is selected, it is difficult to distinguish a region of blood vessels from a region of the contrast agent in a spectral image. Accordingly, it is desirable to select a wavelength combination such that image values corresponding to the contrast agent in a spectral image become less than 60% or greater than 100% from wavelength combinations illustrated in FIG. 7A to FIG. 7D. Furthermore, it is desirable to select a wavelength combination such that image values corresponding to the contrast agent in a spectral image become negative values from the wavelength combinations illustrated in FIG. 7A to FIG. 7D.

Figure 8:
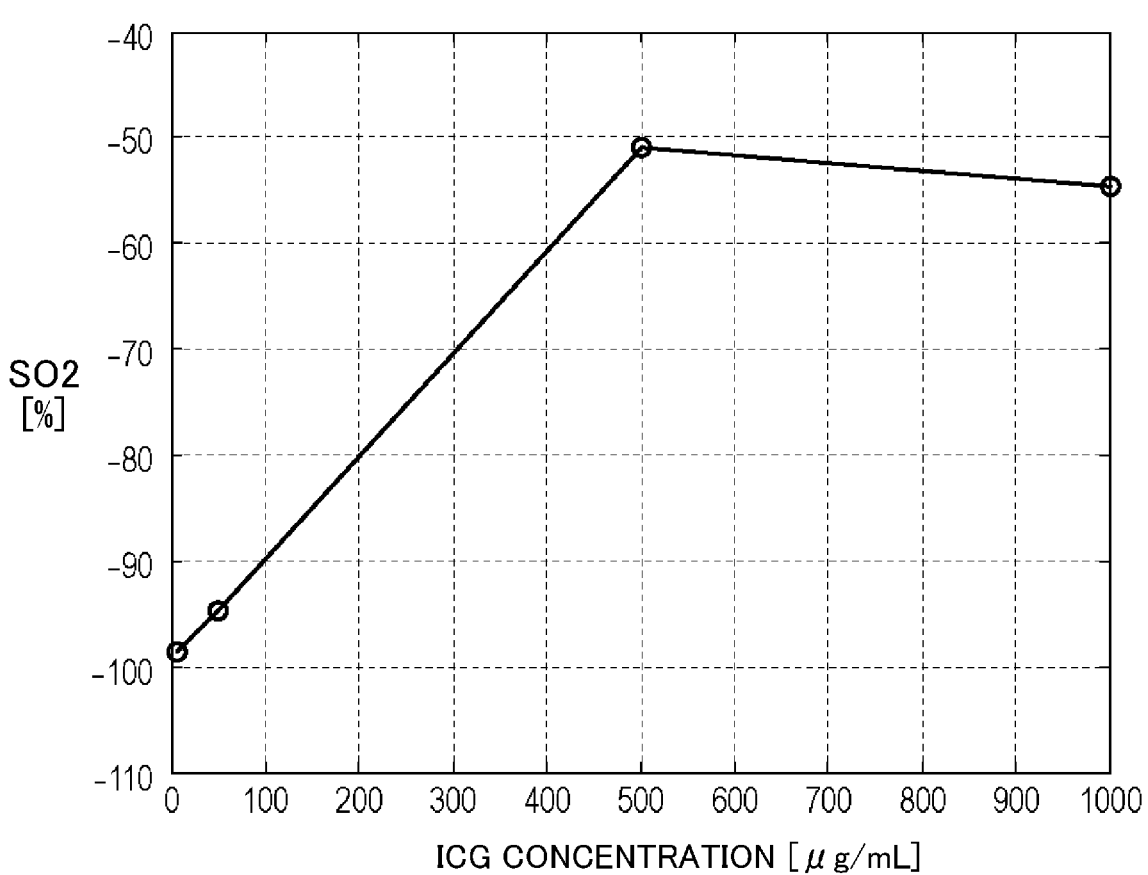
FIG. 8 is a polygonal line graph showing calculation values of formula (1) corresponding the contrast agent when an ICG concentration has been changed.

For example, a case in which 797 nm is selected as a first wavelength and 835 nm is selected as a second wavelength may be conceived here. FIG. 8 is a graph showing a relationship between an ICG concentration and an image value (value of formula (1)) corresponding to a contrast agent in a spectral image in a case where 797 nm is selected as the first wavelength and 835 nm is selected as the second wavelength. According to FIG. 8, in a case where 797 nm is selected as the first wavelength and 835 nm is selected as the second wavelength, image values corresponding to the contrast agent in a spectral image are negative values for any concentration in the range of 5.04 µg/mL to 1.0 mg/mL. Accordingly, in the case of a spectral image generated according to such a wavelength combination, a blood vessel region can be clearly distinguished from a contrast agent region because an oxygen saturation value of blood vessels is not a negative value in principle.

Figure 9:
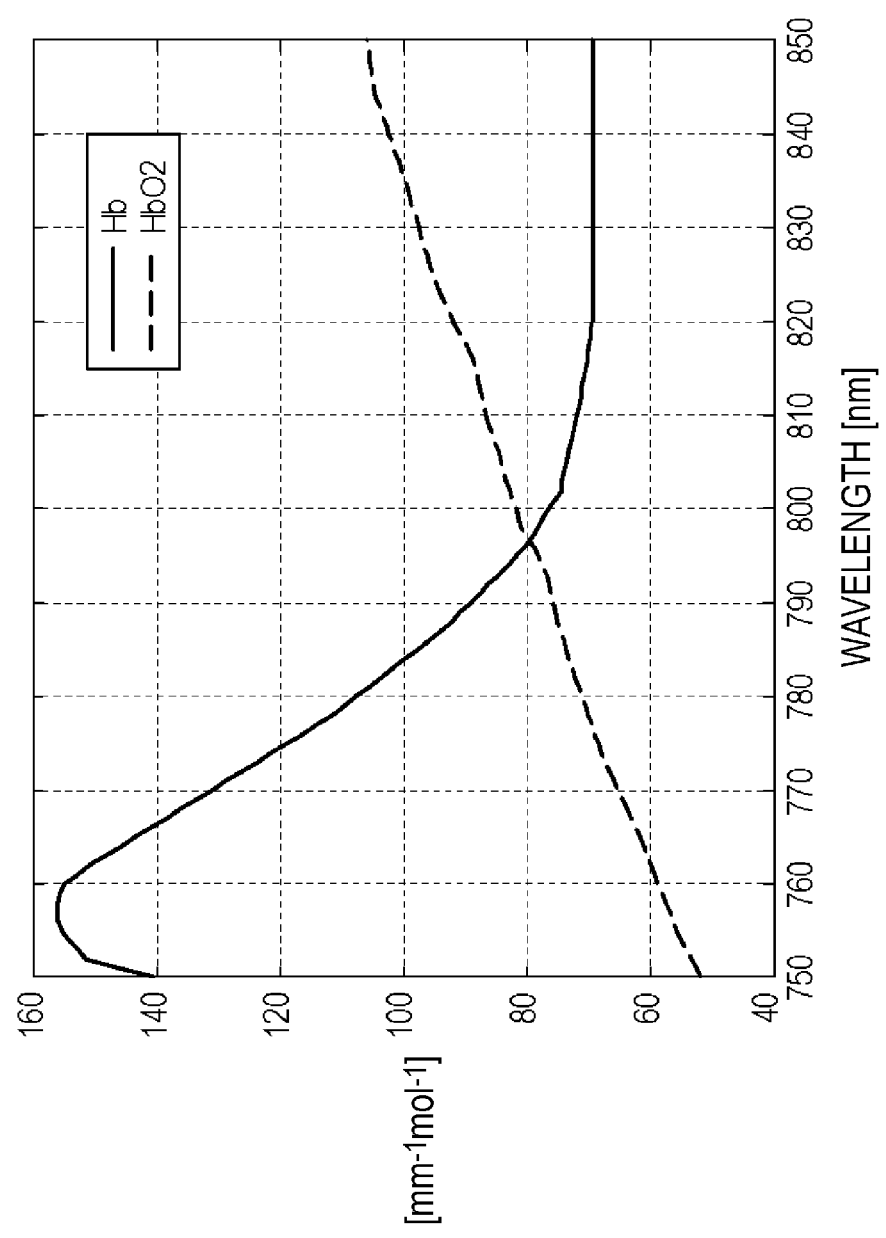
FIG. 9 is a graph showing molar absorption coefficient spectra of oxyhemoglobin and deoxyhemoglobin.

Meanwhile, although determination of wavelengths on the basis of information about a contrast agent has been described, the absorption coefficient of hemoglobin may be considered in determination of wavelengths. FIG. 9 illustrates spectra of the molar absorption coefficient (dotted light) of oxyhemoglobin and the molar absorption coefficient (solid line) of deoxyhemoglobin. In the wavelength range illustrated in FIG. 9, the magnitude relation between the molar absorption coefficient of oxyhemoglobin and the molar absorption coefficient of deoxyhemoglobin is reversed at 797 nm. That is, it can be said that veins are easily recognized at wavelengths shorter than 797 nm and arteries are easily recognized at wavelengths longer than 797 nm. However, in treatment of lymphatic edema, lymphaticovenous anastomosis that generates a bypass between a lymphatic vessel and a vein is used. For this preoperation examination, imaging of both the vein and the lymphatic vessel in which the contrast agent has been accumulated using photoacoustic imaging may be conceived. In this case, it is possible to more clearly image the vein by setting at least one of a plurality of wavelengths to a wavelength shorter than 797 nm. In addition, it is advantageous to set at least one of the plurality of wavelengths to a wavelength at which the molar absorption coefficient of deoxyhemoglobin becomes greater than the molar absorption coefficient of oxyhemoglobin for imaging of the vein. Furthermore, in a case where a spectral image is generated from photoacoustic images corresponding to two wavelengths, it is advantageous to set both the two wavelengths to wavelengths at which the molar absorption coefficient of deoxyhemoglobin is greater than the molar absorption coefficient of oxyhemoglobin for imaging of the vein. By selecting these wavelengths, both a lymphatic vessel into which a contrast agent has been injected and a vein can be imaged with high accuracy in a preoperation examination of lymphaticovenous anastomosis.

However, if all of a plurality of wavelengths are wavelengths at which the absorption coefficient of the contrast agent is greater than that of the blood, oxygen saturation accuracy of the blood decreases due to artifacts derived from the contrast agent. Accordingly, to reduce artifacts derived from the contrast agent, at least one of the plurality of wavelengths may be a wavelength at which the absorption coefficient of the contrast agent is less than the absorption coefficient of the blood.

Here, although a case in which a spectral image is generated according to formula (1) has been described, the present invention can also be applied to cases in which a spectral image is generated such that image values corresponding to a contrast agent in the spectral image change in response to conditions of the contrast agent or the wavelength of radiated light.

(S500: Process of Radiating Light)

The light radiation unit 110 sets the wavelengths determined in S400 in the light source 111. The light source 111 emits lights with the wavelengths determined in S400. The lights generated from the light source 111 are radiated to the object 100 through the optical system 112 as pulsed light. Then, the pulsed light is absorbed in the object 100 to generate photoacoustic waves according to the photoacoustic effect. Here, the injected contrast agent also absorbs the pulsed light to generate photoacoustic waves. The light radiation unit 110 may transmit a synchronization signal to the signal collection unit 140 in addition to transmission of the pulsed light. Further, the light radiation unit 110 performs radiation of light for the plurality of wavelengths in the same manner.

The user may designate control parameters such as radiation conditions (a repetition frequency, wavelength, and the like of radiated light) of the light radiation unit 110 and the position of the probe 180 using the input unit 170. The computer 150 may set control parameters determined on the basis of instruction of the user. In addition, the computer 150 may move the probe 180 to a designated position by controlling the driving unit 130 on the basis of the designated control parameters. In a case where imaging at a plurality of positions is designated, the driving unit 130 moves the probe 180 to an initial designated position first. Meanwhile, the driving unit 130 may move the probe 180 to a position programmed in advance upon a measurement start instruction.

(S600: Process of Receiving Photoacoustic Waves)

The signal collection unit 140 starts a signal collection operation when the synchronization signal transmitted from the light radiation unit 110 is received. That is, the signal collection unit 140 generates an amplified digital electronic signal by performing amplification and AD conversion on an analog electronic signal derived from the photoacoustic waves output from the reception unit 120 and outputs the amplified digital electronic signal to the computer 150. The computer 150 stores the signal transmitted from the signal collection unit 140. In a case where imaging at a plurality of scanning positions is designated, the processes of S500 and S600 are repeatedly executed at the designated scanning positions to repeat radiation of the pulsed light and generation of the digital signal derived from acoustic waves. Meanwhile, the computer 150 may acquire position information of the reception unit 120 at the time of emission of light on the basis of the output from the position sensor of the driving unit 130 using emission of light as a trigger and store the position information.

Meanwhile, although an example in which lights with a plurality of wavelengths are radiated in a time division manner has been described in the present embodiment, a method of radiating light is not limited thereto as long as signal data corresponding to the plurality of wavelengths can be acquired. For example, in a case where encoding is performed using radiation of light, timing at which lights with a plurality of wavelengths are radiated almost simultaneously may be present.

(S700: Process of Generating Photoacoustic Image)

The computer 150 as photoacoustic image acquisition means generates a photoacoustic image on the basis of stored signal data. The computer 150 outputs the generated photoacoustic image to the storage device 1200 such that the photoacoustic image is stored therein.

As a reconstruction algorithm for converting signal data into a two-dimensional or three-dimensional spatial distribution, an analytical reconstruction method such as a back-projection method in the time domain and a back-projection method in the Fourier domain, or a model base method (repeated calculation method) can be employed. For example, universal back-projection (UBP), filtered back-projection (FBP), delay-and-sum, or the like may be conceived as a back-projection method in the time domain.

The computer 150 generates initial sound pressure distribution information (sound pressures generated at a plurality of positions) as a photoacoustic image by performing reconstruction processing on the signal data. In addition, the computer 150 may acquire absorption coefficient distribution information as a photoacoustic image by calculating a light fluence distribution of light radiated to the object 100 in the object 100 and dividing the initial sound pressure distribution by the light fluence distribution. A known method can be applied as a method of calculating the light fluence distribution. In addition, the computer 150 can generate photoacoustic images corresponding to the respective lights with the plurality of wavelengths. Specifically, the computer 150 can generate a first photoacoustic image corresponding to the first wavelength by performing reconstruction processing on signal data acquired through radiation of light with the first wavelength. In addition, the computer 150 can generate a second photoacoustic image corresponding to the second wavelength by performing reconstruction processing on signal data acquired through radiation of light with the second wavelength. In this manner, the computer 150 can generate a plurality of photoacoustic images corresponding to the lights with the plurality of wavelengths.

In the present embodiment, the computer 150 acquires absorption coefficient distribution information corresponding to the lights with the plurality of wavelengths as photoacoustic images. It is assumed that absorption coefficient distribution information corresponding to the first wavelength is a first photoacoustic image and absorption coefficient distribution information corresponding to the second wavelength is a second photoacoustic image.

Meanwhile, although an example in which the system includes the photoacoustic device 1100 that generates photoacoustic images has been described in the present embodiment, the present invention can also be applied to systems that do not include the photoacoustic device 1100. The present invention can be applied to any system as long as the image processing apparatus 1300 as photoacoustic image acquisition means can acquire photoacoustic images. For example, the present invention can also be applied to a system including the storage device 1200 and the image processing apparatus 1300 without the photoacoustic device 1100. In this case, the image processing apparatus 1300 as photoacoustic image acquisition means can read a designated photoacoustic image from a photoacoustic image group stored in advance in the storage device 1200 to acquire the photoacoustic image.

(S800: Process of Generating Spectral Image)

The computer 150 as spectral image acquisition means generates a spectral image on the basis of a plurality of photoacoustic images corresponding to the plurality of wavelengths. The computer 150 outputs the spectral image to the storage device 1200 and causes the storage device 1200 stores the spectral image. As described above, the computer 150 may generate, as a spectral image, an image representing information corresponding concentrations of materials constituting the object, such as a glucose concentration, a collagen concentration, a melanin concentration, and a volume fraction of fat or water. In addition, the computer 150 may generate, as a spectral image, an image representing a ratio of the first photoacoustic image corresponding to the first wavelength to the second photoacoustic image corresponding to the second wavelength. In the present embodiment, an example in which the computer 150 generates an oxygen saturation image as a spectral image according to formula (1) using the first photoacoustic image and the second photoacoustic image is described.

Meanwhile, the image processing apparatus 1300 as spectral image acquisition means may read a designated spectral image from a spectral image group stored in advance in the storage device 1200 to acquire the spectral image. In addition, the image processing apparatus 1300 as photoacoustic image acquisition means may read at least one of a plurality of photoacoustic images used to generate the read spectral image from a photoacoustic image group stored in advance in the storage device 1200 to acquire the photoacoustic image.

(S900: Process of Acquiring Information about Contrast Agent on the Basis of Photoacoustic Image or Spectral Image)

The image processing apparatus 1300 as contrast agent information acquisition means reads a photoacoustic image or a spectral image from the storage device 1200 and acquires information about a contrast agent on the basis of the photoacoustic image or the spectral image.

The information about the contrast agent acquired in S200 is likely not to correspond to conditions of the contrast agent that has been actually injected into the object 100 and has spread into the object 100. Accordingly, the image processing apparatus 1300 may execute image processing on the photoacoustic image or the spectral image and calculate information about a contrast agent from the photoacoustic image or the spectral image. Accordingly, it is possible to acquire information about the contrast agent that has spread into the object 100 from an image obtained by capturing the object 100 in a state in which the contrast agent has been injected into the object 100.

An example of estimating a contrast agent concentration according to image processing performed on a photoacoustic image in a case where an absorption coefficient distribution image is used as the photoacoustic image and an image having the value of formula (1) is used as a spectral image will be described. First, a user indicates a position of a contrast agent concentration that the user wants to obtain in the photoacoustic image or the spectral image. The image processing apparatus 1300 acquires an image value of the photoacoustic image at the designated position. In addition, the image processing apparatus 1300 acquires absorption coefficients of the contrast agent in respective concentrations corresponding to the wavelengths of radiated lights with reference to the absorption coefficient spectrum illustrated in FIG. 6. Here, the image processing apparatus 1300 can determine a type of a contrast agent for which absorption coefficients will be acquired on the basis of the information on the contrast agent type acquired in S200. Then, the image processing apparatus 1300 compares the absorption coefficients of the contrast agent in the respective concentrations with the image value of the photoacoustic image and acquires a contrast agent concentration having a smaller difference from the image value as information about the contrast agent. Meanwhile, the image processing apparatus 1300 may calculate, as information about the contrast agent, a concentration in a case where a norm indicating a difference between an absorption coefficient of the contrast agent and the image value of the photoacoustic image is less than a predetermined value according to a least squares method.

In addition, an example of estimating a contrast agent concentration according to image processing performed on a spectral image will be described. The image processing apparatus 1300 acquires an image value of the spectral image at a designated position. In addition, the image processing apparatus 1300 acquires absorption coefficients of the contrast agents in respective concentrations corresponding to two wavelengths of radiated lights with reference to the absorption coefficient spectrum illustrated in FIG. 6. Further, the image processing apparatus 1300 calculates a value corresponding to each concentration according to formula (1) on the basis of the absorption coefficient corresponding to each concentration. Then, the image processing apparatus 1300 compares the value of formula (1) corresponding to each concentration with the image value of the spectral image and acquires a contrast agent concentration having a smaller difference from the image value as information about the contrast agent. Meanwhile, the image processing apparatus 1300 may calculate, as information about the contrast agent, a concentration in a case where a norm indicating a difference between the calculated value of formula (1) and the image value of the spectral image is less than a predetermined value according to a least squares method.

In addition, the computer 150 may read information about a contrast agent stored as supplementary information associated with a photoacoustic image or a spectral image to acquire the information about the contrast agent. For example, the computer 150 can read information about a contrast agent stored in a tag of a photoacoustic image or a spectral image as a DICOM image to read the information about the contrast agent. According to this aspect, the image processing apparatus 1300 can read an image from the storage device 1200 such as a PACS and perform setting of image display and setting of wavelengths depending on conditions of a contrast agent associated with the image even when measurement of photoacoustic waves is not accompanied.

Meanwhile, the image processing apparatus 1300 may read a contrast agent type from supplementary information associated with an image and calculate a contrast agent concentration through image processing on the image. In this manner, the image processing apparatus 1300 may acquire a plurality of pieces of information about a contrast agent through a combination of different methods.

(S1000: Process of Determining Whether to Reset Wavelengths)

The image processing apparatus 1300 determines whether to reset wavelengths. The procedure returns to S400 if the image processing apparatus 1300 determines that the wavelengths are reset and proceeds to S1100 if the image processing apparatus 1300 determines that the wavelengths are not reset.

For example, the image processing apparatus 1300 determines that the wavelengths are reset in a case where instruction for resetting the wavelengths is received from the user. Here, the image processing apparatus 1300 may cause the display device 1400 to display the information about the contrast agent acquired in S900. Then, the user may check the information displayed on the display device 1400 and instruct resetting of the wavelengths using the input device 1500 upon determining that resetting of the wavelengths is necessary. In a case where the instruction for resetting of the wavelengths is received through the input device 1500, the image processing apparatus 1300 may determine that resetting of the wavelengths is performed and cause the computer 150 to execute resetting of the wavelengths. Meanwhile, the user may indicate wavelengths of radiated light themselves as an instruction for resetting the wavelengths.

In addition, the image processing apparatus 1300 may compare the information about the contrast agent acquired in S200 with the information about the contrast agent acquired in S900 and determine that the wavelengths are reset if there is a difference between the pieces of information.

Furthermore, the image processing apparatus 1300 may compare the information about the contrast agent acquired in S200 with the information about the contrast agent acquired in S900, and if there is a difference between the pieces of information, cause the display device 1400 to display this fact. In addition, the image processing apparatus 1300 may cause information about the contrast agent having a difference to be displayed. The user may check the information displayed on the display device 1400 and instruct resetting of the wavelengths using the input device 1500 upon determining that resetting of the wavelength is necessary. That is, the image processing apparatus 1300 may cause the display device 1400 to display information based on the information about the contrast agent acquired in S900.

On the other hand, in a case where the image processing apparatus 1300 does not determine that the wavelengths are reset, the procedure proceeds to S1100. For example, the image processing apparatus 1300 may determine that resetting of the wavelengths is not performed in a case where instruction for resetting the wavelength has not been received from the user for a specific time. In addition, the image processing apparatus 1300 may determine that resetting of the wavelengths is not performed in a case where an instruction indicating that resetting of wavelength is not performed has been received from the user. Further, the image processing apparatus 1300 may determine that resetting of the wavelengths is not performed in a case where the information about the contrast agent acquired in S200 and the information about the contrast agent acquired in S900 do not have a difference therebetween. The image processing apparatus 1300 may determine that resetting of the wavelengths is not performed in a case where at least one of these conditions has been received.

(S1100: Process of Displaying Spectral Image)

The image processing apparatus 1300 as display control means causes the display device 1400 to display a spectral image such that a region corresponding to the contrast agent can be distinguished from other regions on the basis of the information about the contrast agent acquired in S200 or S900. Meanwhile, as a rendering method, any method such as maximum intensity projection (MIP), volume rendering, and surface rendering can be employed. Here, setting conditions such as a display area and a sight direction at the time of rendering a three-dimensional image in two dimensions can be arbitrarily designated in accordance with an observation target.

Here, a case in which 797 nm and 835 nm are set in S400 and a spectral image is generated according to formula (1)

in S800 will be described. As illustrated in FIG. 8, in a case where these two wavelengths are selected, an image value corresponding to the contrast agent in the spectral image generated according to formula (1) is a negative value at any concentration of ICG.

As illustrated in FIG. 10, the image processing apparatus 1300 displays a color bar 2400 as a color scale indicating a relation between an image value and a display color of a spectral image on the GUI. The image processing apparatus 1300 may determine a numerical value range of image values allocated to the color scale on the basis of the information about the contrast agent (e.g., information representing that a contrast agent type is ICG) and information representing wavelengths of radiated lights. For example, the image processing apparatus 1300 may determine a numerical value range including oxygen saturations of arteries, oxygen saturations of veins, and image values that are negative values corresponding to the contrast agent according to formula (1). The image processing apparatus 1300 may determine a numerical value range of −100% to 100% and set the color bar 2400 in which −100% to 100% are allocated to color gradation changing from blue to red. According to this display method, it is possible to identify arteriovenous and also identify a region corresponding to the contrast agent, which has a negative value. In addition, the image processing apparatus 1300 may display an indicator 2410 indicating a numerical value range of image values corresponding to the contrast agent on the basis of the information about the contrast agent and the information representing the wavelengths of radiated lights. Here, a region having negative values is indicated using the indicator 2410 as a numerical value range of image values corresponding to ICG in the color bar 2400. By displaying the color scale such that a display color corresponding to the contrast agent can be identified in this manner, it is possible to easily identify a region corresponding to the contrast agent in a spectral image.

The image processing apparatus 1300 as region determination means may determine a region corresponding to the contrast agent in a spectral image on the basis of the information about the contrast agent and the information representing the wavelengths of radiated lights. For example, the image processing apparatus 1300 may determine a region having negative image values in the spectral image as the region corresponding to the contrast agent. Then, the image processing apparatus 1300 may cause the display device 1400 to display the spectral image such that the region corresponding to the contrast agent can be distinguished from other regions. The image processing apparatus 1300 can employ identification display such as making a display color of the region corresponding to the contrast agent different from a display color of other regions, blinking the region corresponding to the contrast agent, or displaying an indicator (e.g., a frame) indicating the region corresponding to the contrast agent.

Meanwhile, an item 2730 corresponding to display of ICG displayed on the GUI illustrated in FIG. 10 may be indicated to switch to a display mode in which an image value corresponding to ICG is selectively displayed. For example, in a case where the user selects the item 2730 corresponding to display of ICG, the image processing apparatus 1300 may selectively display the region of ICG by selecting voxels having negative image values from the spectral image and selectively rendering the selected voxels. Likewise, the user may select an item 2710 corresponding to display of arteries or an item 2720 corresponding to display of veins. The image processing apparatus 1300 may switch to a display mode in which image values (e.g., at least 90% and not more than 100%) corresponding to arteries or image values (e.g., at least 60% and not more than 90%) corresponding to veins are selectively displayed on the basis of instruction of the user. Numerical value ranges of image values corresponding to arteries and image values corresponding to veins may be changed on the basis of instruction of the user.

Meanwhile, images obtained by allocating at least one of hue, brightness, and chroma to an image value of a spectral image and allocating the remaining parameters of the hue, brightness, and chroma to an image value of a photoacoustic image may be displayed as spectral images. For example, images obtained by allocating hue and chroma to an image value of a spectral image and allocating brightness to an image value of a photoacoustic image may be displayed as spectral images. Here, when an image value of the photoacoustic image corresponding to a contrast agent is greater than or less than an image value of the photoacoustic image corresponding to blood vessels, there are cases in which it is difficult to visually recognize both the blood vessels and the contrast agent when brightnesses are allocated to image values of the photoacoustic image. Accordingly, a conversion table for conversion from the image values of the photoacoustic image to brightnesses may be changed in response to image values of the spectral image. For example, in a case where the image values of the spectral image are included in a numerical value range of image values corresponding to the contrast agent, brightnesses corresponding to the image values of the photoacoustic image may be less than those corresponding to the blood vessels. That is, if the image values of the photoacoustic image are identical when the region of the contrast agent is compared with the region of the blood vessels, the brightness of the region of the contrast agent may be decreased to be less than that of the region of the blood vessels. Here, the conversion table is a table representing brightnesses corresponding to a plurality of image values. In addition, in a case where the image values of the spectral image are included in the numerical value range of the image values corresponding to the contrast agent, brightnesses corresponding to the image values of the photoacoustic image may be increased to be greater than those corresponding to the blood vessels. That is, if the image values of the photoacoustic image are identical when the region of the contrast agent is compared with the region of the blood vessels, the brightness of the region of the contrast agent may be increased to be greater than that of the region of the blood vessels. In addition, a numerical value range of image values of the photoacoustic image in which the image values of the photoacoustic image are not converted into brightnesses may vary according to the image values of the spectral image.

The conversion table may be changed to a suitable one according to the type and concentration of a contrast agent or the wavelength of radiated light. Accordingly, the image processing apparatus 1300 may determine a conversion table for conversion from image values of a photoacoustic image to brightnesses on the basis of information about a contrast agent and information representing the wavelength of radiate light. In a case where it is estimated that image values of a photoacoustic image corresponding to a contrast agent are greater than those corresponding to blood vessels, the image processing apparatus 1300 may decrease brightnesses corresponding to the image values of the photoacoustic image corresponding to the contrast agent to be less than those corresponding to the blood vessels. On the other hand, in a case where it is estimated that the image values of the photoacoustic image corresponding to the contrast agent are less than those corresponding to the blood vessels, the image processing apparatus 1300 may increase the brightnesses corresponding to the image values of the photoacoustic image corresponding to the contrast agent to be greater than those corresponding to the blood vessels.

The GUI illustrated in FIG. 10 displays an absorption coefficient image (first photoacoustic image) 2100 corresponding to a wavelength of 797 nm, an absorption coefficient image (second photoacoustic image) 2200 corresponding to a wavelength of 835 nm, and an oxygen saturation image (spectral image) 2300. The GUI may display light with wavelengths used to generate the respective images. Although both a photoacoustic image and a spectral image are displayed in the present embodiment, only the spectral image may be displayed. In addition, the image processing apparatus 1300 may switch between display of the photoacoustic image and display of the spectral image on the basis of instruction of the user.

Meanwhile, the display unit 160 may display a moving image. For example, a configuration in which the image processing apparatus 1300 generates at least any of the first photoacoustic image 2100, the second photoacoustic image 2200, and the spectral image 2300 in a time series, generates moving image data on the basis of the generated time-series image and outputs the moving image data to the display unit 160 may be employed. Meanwhile, it is desirable that a still image or a time-compressed moving image be displayed in order to reduce a determination time of a user in view of a relatively small number of times of lymph flowing. In addition, in display of a moving image, a lymph flowing state can be repeatedly displayed. A moving image speed may be a predetermined speed defined in advance or a predetermined speed designated by a user.

In addition, in the display unit 160 capable of displaying moving images, it is desirable that a frame rate of moving images be variable. To set a variable frame rate, a window for a user to manually input a frame rate, a slide bar for changing frame rates, or the like may be added to the GUI of FIG. 10. Here, since lymph intermittently flows in lymphatic vessels, only a part of acquired time-series volume data can be used to check lymph flow. Accordingly, there are cases in which efficiency decreases when real-time display is performed at the time of checking lymph flow. Therefore, a moving image can be displayed in a fast-forward manner and a user can check a state of fluid in lymphatic vessels within a short time by setting a variable frame rate of moving images displayed on the display unit 160.

In addition, the display unit 160 may repeatedly display a moving image within a predetermined time range. Here, it is also desirable to add a GUI such as a window or a slide bar by which a user can designate a range in which repeated display is performed to FIG. 10. Accordingly, the user can easily ascertain a state of fluid flowing in lymphatic vessels, for example.

As described above, at least one of the image processing apparatus 1300 and the computer 150 as an information processing device serves as a device including at least one of spectral image acquisition means, contrast agent information acquisition means, region determination means, photoacoustic image acquisition means, and display control means. Meanwhile, the respective means may be configured as different pieces of hardware or as a single piece of hardware. In addition, a plurality of means may be configured as a single piece of hardware.

Although it is possible to distinguish a contrast agent from blood vessels by selecting a wavelength at which a value according to formula (1) corresponding to the contrast agent becomes a negative value in the present embodiment, an image value corresponding to the contrast agent may be any value as long as the contrast agent can be distinguished from the blood vessels using the image value corresponding to the contrast agent. For example, in a case where an image value of a spectral image (oxygen saturation image) corresponding to the contrast agent is less than 60% or greater than 100%, and the like, image processing described in the present processes can also be applied.

Although an example of a case in which ICG is used as a contrast agent has been described in the present embodiment, image processing according to the present embodiment may be applied to any contrast agent other than ICG. In addition, the image processing apparatus 1300 may execute image processing depending on a contrast agent type on the basis of information about the type of a contrast agent injected into the object 100 among a plurality of types of contrast agents.

A case in which an image processing method is determined on the basis of acquired information about a contrast agent among a plurality of pieces of information about a contrast agent has been described in the present embodiment. However, in a case in which conditions of a contrast agent used for imaging have been uniquely determined, image processing corresponding to the conditions of the contrast agent may be set in advance. In this case, the above-described image processing according to the present embodiment can also be applied.

Although an example of applying image processing to a spectral image based on photoacoustic images corresponding to a plurality of wavelengths has been described in the present embodiment, image processing according to the present embodiment may be applied to a photoacoustic image corresponding to a single wavelength. That is, the image processing apparatus 1300 may determine a region corresponding to a contrast agent in a photoacoustic image on the basis of information about the contrast agent and display the photoacoustic image such that the region corresponding to the contrast agent can be distinguished from other regions. In addition, the image processing apparatus 1300 may display a spectral image or a photoacoustic image such that a region having a numerical value range of preset image values corresponding to a contrast agent can be distinguished from other regions.

Although an example in which the computer 150 as an information processing device radiates lights with a plurality of wavelengths to generate a spectral image has been described in the present embodiment, a wavelength may be determined through the wavelength determination method according to the present embodiment in a case in which only light with a single wavelength is radiated to generate a photoacoustic image. That is, the computer 150 may determine a wavelength of radiated light on the basis of information about a contrast agent. In this case, it is desirable that the computer 150 determine a wavelength such that an image value of a region of the contrast agent in a photoacoustic image can be distinguished from an image value of a region of blood vessels.

Meanwhile, the light radiation unit 110 may radiate light with a wavelength set in advance such that an image value of a region of a contrast agent in a photoacoustic image can be distinguished from an image value of a region of blood vessels to the object 100. In addition, the light radiation unit 110 may radiate lights with a plurality of wavelengths set in advance such that an image value of a region of a contrast agent in a photoacoustic image can be distinguished from an image value of a region of blood vessels to the object 100.

According to the present invention, it is possible to provide an image processing apparatus for generating a display image through which a structure of a contrasting target is easily ascertained through photoacoustic imaging.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

The present invention is not limited to the above-described embodiments and can be modified and changed in various manners without departing from the spirit and scope of the present invention. Accordingly, the following claims are annexed in order to officially announce the scope of the present invention.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. An image processing apparatus comprising:

a memory storing a program; and one or more processors which, by executing the program, function as a plurality of units comprising:

(1) a spectral image signal acquisition unit configured to acquire a single spectral image signal by performing a common calculation processing on both of (a) a first photoacoustic signal obtained by irradiating an object with light of a first wavelength and (b) a second photoacoustic signal obtained by irradiating the object with light of a second wavelength different from the first wavelength, wherein the common calculation processing includes a common formula using both of the first photoacoustic signal and the second photoacoustic signal, and wherein as a result of the common calculation processing, the single spectral image signal has (a) a first numerical value range corresponding to the contrast agent, (b) a second numerical value range corresponding to oxyhemoglobin, and (c) a third numerical value range corresponding to deoxyhemoglobin;

(2) a region determination unit configured to (a) determine a region of the single spectral image signal having the first numerical value range in the single spectral image signal as a lymphatic vessel region, (b) determine a region of the single spectral image signal having the second numerical value range in the single spectral image signal as an artery region, and (c) determine a region of the single spectral image signal having the third numeral value range in the single spectral image signal as a vein region; and (3) a display control unit configured to display the single spectral image signal in a manner based on image values of the single spectral image signal included in the first numerical value range, the second numerical value range, and the third numerical value range such that the lymphatic vessel region, the artery region, and the vein region are distinguishable from each other, wherein the first wavelength and the second wavelength are set such that the first numerical value range, the second numerical value range, and the third numerical value range are different from one another.

2. The image processing apparatus according to claim 1, wherein the region determination unit is configured to:

determine the first numerical value range on the basis of information about the contrast agent, and determine a region of the single spectral image having image values included in the first numerical value range as a region corresponding to the contrast agent.

3. The image processing apparatus according to claim 1, wherein the region determination unit is configured to determine the first numerical value range for image values of the single spectral image to which colors are allocated on the basis of information about the contrast agent, and wherein the display control unit is configured to allocate colors to image values of the single spectral image signal included in the first numerical value range and to display the single spectral image.

4. The image processing apparatus according to claim 1, wherein the image processing apparatus is configured such that a sign of an image value in the first numerical value range and a sign of an image value in the second numerical value range are different.

5. The image processing apparatus according to claim 1, wherein the region determination unit is configured to determine the region corresponding to the contrast agent in the single spectral image signal on the basis of information about the contrast agent and information on the plurality of wavelengths.

6. An image processing apparatus comprising:

a memory storing a program; and one or more processors which, by executing the program, function as a plurality of units comprising:

(1) a spectral image signal acquisition unit configured to a acquire a single spectral image signal by performing a common calculation processing on both of (a) a first photoacoustic signal obtained by irradiating an object with light of a first wavelength and (b) a second photoacoustic signal obtained by irradiating the object with light of a second wavelength different from the first wavelength, wherein the common calculation processing includes a common formula using both of the first photoacoustic signal and the second photoacoustic signal, and wherein as a result of the common calculation processing, the single spectral image signal has (a) a first numerical value range corresponding to the contrast agent, (b) a second numerical value range corresponding to oxyhemoglobin, and (c) a third numerical value range corresponding to deoxyhemoglobin;

(2) a region determination unit configured to (a) determine a region of the single spectral image signal having the first numerical value range in the single spectral image signal as a lymphatic vessel region, (b) determine a region of the single spectral image signal having the second numerical value range in the single spectral image signal as an artery region, and (c) determine a region of the single spectral image signal having the third numeral value range in the single spectral image signal as a vein region; and (3) a display control unit configured to allocate different colors to image values of the single spectral image signal included in the first numerical value range, the second numerical value range, and the third numerical value range and to display the single spectral image signal in which the lymphatic vessel region, the artery region, and the vein region are displayed in the different colors to be distinguishable from each other, wherein the first wavelength and the second wavelength are set such that the first numerical value range, the second numerical value range, and the third numerical value range are different from one another.

7. The image processing apparatus according to claim 6, wherein the display control unit is configured to allocate colors to image values of the single spectral image signal and displays the single spectral image signal on the basis of information about the contrast agent and information on the plurality of wavelengths.

8. The image processing apparatus according to claim 1, wherein the display control unit is configured to:

display a color scale indicating a relation between image values and display colors of the single spectral image signal, and display the color scale such that a display color corresponding to the contrast agent is able to be identified.

9. The image processing apparatus according to claim 1, wherein the spectral image signal acquisition unit is configured to acquire the single spectral image signal by radiating lights with the plurality of wavelengths to the object into which the contrast agent has been injected, and wherein the display control unit is configured to:

(1) determine a brightness of the single spectral image signal on the basis of image values of the single spectral image signal, and (2) determine a conversion table for conversion from image values of the single spectral image signal into brightness on the basis of image values of the single spectral image signal.

10. The image processing apparatus according to claim 1, wherein the spectral image signal acquisition unit is configured to (1) acquire a first photoacoustic image based on photoacoustic waves generated according to radiation of light with a first wavelength and a second photoacoustic image based on photoacoustic waves generated according to radiation of light with a second wavelength, and (2) generate an image signal based on a ratio of the first photoacoustic image to the second photoacoustic image as the single spectral image signal.

11. The image processing apparatus according to claim 1, wherein, in a case where a measured value based on photoacoustic waves generated according to radiation of light with a first wavelength $\lambda_1$ of the plurality of different wavelengths is $I^{\lambda}{}_1(r)$, a measured value based on photoacoustic waves generated according to radiation of light with a second wavelength $\lambda_2$ of the plurality of different wavelengths is $I^{\lambda}{}_2(r)$, a molar absorption coefficient of deoxyhemoglobin corresponding to the first wavelength $\lambda_1$ is $\varepsilon_{Hb}{}^{\lambda}{}_1$, absorption coefficient of deoxyhemoglobin corresponding to the second wavelength $\lambda_2$ is $\varepsilon_{Hb}{}^{\lambda}{}_2$, a molar absorption coefficient of oxyhemoglobin corresponding to the first wavelength $\lambda_1$ is $\varepsilon_{HbO}{}^{\lambda}{}_1$, a molar absorption coefficient of oxyhemoglobin corresponding to the second wavelength $\lambda_2$ is $\varepsilon_{HbO}{}^{\lambda}{}_2$, and r is a position, the spectral image signal acquisition unit is configured to generate a calculated value Is(r) of the single spectral image signal according to the following formula:

$$Is(r) = \frac{\frac{I^{\lambda_2}(r)}{I^{\lambda_1}(r)} \cdot \varepsilon_{Hb}^{\lambda_1} - \varepsilon_{Hb}^{\lambda_2}}{\left(\varepsilon_{HbO}^{\lambda_2} - \varepsilon_{Hb}^{\lambda_2}\right) - \frac{I^{\lambda_2}(r)}{I^{\lambda_1}(r)} \cdot \left(\varepsilon_{HbO}^{\lambda_1} - \varepsilon_{Hb}^{\lambda_1}\right)} \qquad \text{[Math. 1]}$$

12. The image processing apparatus according to claim 11, wherein the measured values are absorption coefficients or initial sound pressures.

13. The image processing apparatus according to claim 1, wherein the contrast agent is indocyanine green (ICG) having a concentration of at least 2.5 mg/mL and not more than 10.0 mg/mL.

14. The image processing apparatus according to claim 1, wherein information representing a concentration of the contrast agent is acquired as information about the contrast agent on the basis of an instruction from a user, and wherein in a case where information representing that a type of the contrast agent is indocyanine green (ICG) is acquired as the information about the contrast agent, an instruction from the user which indicates an ICG concentration less than 2.5 mg/mL or greater than 10.0 mg/mL is not received.

15. The image processing apparatus according to claim 13, wherein the plurality of wavelengths include 797 nm as a first wavelength and 835 nm as a second wavelength.

16. The image processing apparatus according to claim 1, wherein the display control unit is configured to display a plurality of spectral images generated in a time series as a moving image.

17. The image processing apparatus according to claim 16, wherein the display control unit is able to display the moving image in a fast-forward manner.

18. The image processing apparatus according to claim 16, wherein the display control unit is able to repeatedly display the moving image.

19. An image processing method comprising:

acquiring a single spectral image signal by performing a common calculation processing on both of (a) a first photoacoustic signal obtained by irradiating an object with light of a first wavelength and (b) a second photoacoustic signal obtained by irradiating the object with light of a second wavelength different from the first wavelength, wherein the common calculation processing includes a common formula using both of the first photoacoustic signal and the second photoacoustic signal, and wherein as a result of the common calculation processing, the single spectral image signal has (a) a first numerical value range corresponding to the contrast agent, (b) a second numerical value range corresponding to oxyhemoglobin, and (c) a third numerical value range corresponding to deoxyhemoglobin;

determining a region of the single spectral image signal having the first numerical value range in the single spectral image signal as a lymphatic vessel region;

determining a region of the single spectral image signal having the second numerical value range in the single spectral image signal as an artery region;

determining a region of the single spectral image signal having the third numerical value range in the single spectral image signal as a vein region; and displaying the single spectral image signal in a manner based on image values of the single spectral image signal included in the first numerical value range, the second numerical value range, and the third numerical value range such that the lymphatic vessel region, the artery region, and the vein region are distinguishable from each other, wherein the acquiring comprises setting the first wavelength and the second wavelength such that the first numerical value range, the second numerical value range, and the third numerical value range are different from one another.

20. An image processing method comprising:

acquiring a single spectral image signal by performing a common calculation processing on both of (a) a first photoacoustic signal obtained by irradiating an object with light of a first wavelength and (b) a second photoacoustic signal obtained by irradiating the object with light of a second wavelength different from the first wavelength, wherein the common calculation processing includes a common formula using both of the first photoacoustic signal and the second photoacoustic signal, and wherein as a result of the common calculation processing, the single spectral image signal has (a) a first numerical value range corresponding to the contrast agent, (b) a second numerical value range corresponding to oxyhemoglobin, and (c) a third numerical value range corresponding to deoxyhemoglobin;

determining a region of the single spectral image signal having the first numerical value range in the single spectral image signal as a lymphatic vessel region;

determining a region of the single spectral image signal having the second numerical value range in the single spectral image signal as an artery region;

determining a region of the single spectral image signal having the third numerical value range in the single spectral image signal as a vein region;

allocating different colors to image values of the single spectral image signal included in the first numerical value range, the second numerical value range, and the third numerical value range; and displaying the single spectral image signal in which the lymphatic vessel region, the artery region, and the vein region are displayed in the different colors to be distinguishable from each other, wherein the acquiring comprises setting the first wavelength and the second wavelength such that the first numerical value range, the second numerical value range, and the third numerical value range are different from one another.

21. The image processing method according to claim 19, wherein the contrast agent is indocyanine green (ICG) and the plurality of wavelengths include 797 nm as a first wavelength and 835 nm as a second wavelength.

22. A non-transitory computer-readable medium storing a program for causing a computer to execute the image processing method according to claim 19.

23. A non-transitory computer-readable medium storing a program for causing a computer to execute the image processing method according to claim 20.

24. The image processing apparatus according to claim 1, wherein at least one of the first wavelength and the second wavelength is a wavelength at which the molar absorption coefficient of deoxyhemoglobin becomes greater than the molar absorption coefficient of oxyhemoglobin for imaging of a vein.

25. The image processing apparatus according to claim 1, wherein each of the first wavelength and the second wavelength is a wavelength at which the molar absorption coefficient of deoxyhemoglobin becomes greater than the molar absorption coefficient of oxyhemoglobin for imaging of a vein.

26. The image processing apparatus according to claim 1, wherein at least one of the first wavelength and the second wavelength is a wavelength at which the absorption coefficient of the contrast agent is less than the absorption coefficient of the blood.

27. The information processing apparatus according to claim 1, wherein a calculated value Is(r) of the single spectral image signal is determined as a function of a ratio of (a) a measured value based on photoacoustic waves generated according to radiation of light with the second wavelength and (b) a measured value based on photoacoustic waves generated according to radiation of light with the first wavelength.

28. The information processing apparatus according to claim 27, wherein the calculated value Is(r) is determined as a function of (1) the ratio of (a) a measured value based on photoacoustic waves generated according to radiation of light with the second wavelength and (b) a measured value based on photoacoustic waves generated according to radiation of light with the first wavelength and (2) a value determined by taking the negative of that ratio.

29. The information processing apparatus according to claim 28, wherein the first wavelength and the second wavelength are both wavelengths at which a molar absorption coefficient of deoxyhemoglobin is greater than a molar absorption coefficient of oxyhemoglobin, and wherein at least one of the first wavelength and the second wavelength is a wavelength at which an absorption coefficient of the contrast agent is less than an absorption coefficient of blood.

30. The information processing apparatus according to claim 28, wherein the first numerical value range corresponding to the contrast agent includes both (a) values that are smaller than those within the second numerical value range corresponding to oxyhemoglobin and (b) values that are larger than those within the second numerical value range corresponding to oxyhemoglobin and the third numerical value range corresponding to deoxyhemoglobin.

31. The information processing apparatus according to claim 28, wherein the first numerical value range corresponding to the contrast agent has a sign opposite to that of the second numerical value range corresponding to oxyhemoglobin and the third numerical value range corresponding to deoxyhemoglobin.

* * * * *